United States Patent
Wang et al.

(10) Patent No.: US 7,141,540 B2
(45) Date of Patent: Nov. 28, 2006

(54) CYCLODEXTRIN GRAFTED BIOCOMPATIBLE AMPHILPHILIC POLYMER AND METHODS OF PREPARATION AND USE THEREOF

(75) Inventors: Laixin Wang, Salt Lake City, UT (US); Duane E. Ruffner, Salt Lake City, UT (US)

(73) Assignee: Genta Salus LLC, Berkeley Heights, NJ (US)

( * ) Notice: Subject to any disclaimer, the term of this patent is extended or adjusted under 35 U.S.C. 154(b) by 462 days.

(21) Appl. No.: 09/999,252

(22) Filed: Nov. 30, 2001

(65) Prior Publication Data

US 2003/0144222 A1 Jul. 31, 2003

(51) Int. Cl.
- A61K 31/00 (2006.01)
- A61K 31/70 (2006.01)
- A61K 31/555 (2006.01)
- A61K 31/38 (2006.01)

(52) U.S. Cl. ................. 514/1; 514/2; 514/44; 514/185; 514/449; 527/300

(58) Field of Classification Search ............... 514/1, 514/2, 44, 185, 449; 527/300
See application file for complete search history.

(56) References Cited

U.S. PATENT DOCUMENTS

| | | | |
|---|---|---|---|
| 4,869,904 A | 9/1989 | Uekama et al. |
| 5,134,127 A | 7/1992 | Stella et al. |
| 5,376,645 A | 12/1994 | Stella et al. |
| 5,403,898 A | 4/1995 | Bradshaw et al. |
| 5,473,055 A | 12/1995 | Mongelli et al. |
| 5,569,720 A | 10/1996 | Mongelli et al. |
| 5,624,940 A | 4/1997 | Bryant et al. |
| 5,633,368 A | 5/1997 | Hirsenkorn |
| 5,654,422 A | 8/1997 | Hirsenkorn |
| 5,874,418 A | 2/1999 | Stella et al. |
| 5,904,929 A | 5/1999 | Uekama et al. |
| 5,916,883 A | 6/1999 | Shalaby et al. |
| 6,046,177 A | 4/2000 | Stella et al. |
| 6,048,736 A | 4/2000 | Kosak |
| 6,133,248 A | 10/2000 | Stella |
| 2001/0021703 A1 | 9/2001 | Kosak |
| 2001/0034333 A1 | 10/2001 | Kosak |

FOREIGN PATENT DOCUMENTS

| | | |
|---|---|---|
| EP | 0730869 | 9/1996 |
| FR | PCT/FR00/00377 | 2/2000 |
| WO | WO 00/01734 | 1/2000 |
| WO | WO 00/47630 | 8/2000 |
| WO | WO 04/22099 | 3/2004 |

OTHER PUBLICATIONS

S.H. Hwang, N.C. Bellocq & M.E. Davis "Effects of Structure of β–Cyclodextrin–Containing Polymers on Gene Delivery," *Bioconjug. Chem.*, Mar.–Apr. 2001; 12(2):280–90.

Hector Gonzales, Sue Jean Hwang and M.E. Davis, "New Class of Polymers for the Delivery of Macromolecular Therapeutics," *Biogonjug. Chem.*, Nov.–Dec. 1999; 10(6):1068–74.

(Continued)

*Primary Examiner*—Richard Schnizer
(74) *Attorney, Agent, or Firm*—Kenyon & Kenyon LLP

(57) ABSTRACT

Amphiphilic biocompatible cyclodextrin grafted polymers comprising a hydrophobically modified cyclodextrin moiety, a linear linker and a biocompatible hydrophilic polymer backbone, wherein said cyclodextrin moiety is grafted to said biocompatible hydrophilic polymer backbone by said linker are disclosed. The cyclodextrin-grafted biocompatible polymers of this invention may be used as bioactive agent carriers. Methods of making and using such cyclodextrin-grafted biocompatible polymers are disclosed.

30 Claims, 6 Drawing Sheets

OTHER PUBLICATIONS

Kouzou Miyake, Fumitoshi Hirayama & Kaneto Ueckama, "Solubility and Mass and Nuclear Magnetic Resonance Spectroscopic Studies on Interaction of Cyclosporin A With Dimethyl-α- and -β-Cyclodextrins in Aqueous Solution," *Journal of Pharmaceutical Sciences*, vol. 88, No. 1, Jan. 1999, pp. 39-45.

Benito Casu, Mario Reggiani, "Methylated Cycloamyloses (Cyclodextrins) and Their Inclusion Properties," *Carbohydr. Res.*, 76, 59-66 (1979).

Alan P. Croft & Richard A. Bartsch, Synthesis of Chemically Modified Cyclodextrins, *Tetrahedron*, vol. 39, No. 9, Great Britain, pp. 1417-1474 (1983).

same as AR.

Uma S. Sharma, Sathyamangalam V. Balasubramanian & Robert M. Straubinger, "Pharmaceutical and Physical Properties of Paclitaxel (Taxol) Complexes with Cyclodextrins," *Journal of Pharmaceutical Sciences*, vol. 84, No. 10, Oct. 1995, pp. 1223-1230.

M. Pechar, K. Ulbrich, V. Subr, "Poly(ethylene Glycol) Multiblock Copolymer As A Carrier of Anti-Cancer Drug Doxorubicin," *Bioconjugate Chem.*, 2000, Mar. Apr. 11(2): 131-9.

Arima, Hidetoshi et al., Enhancement of gene expression by polyamidoamine dendrimer conjugates with α-, β-, and γ-cyclotrines, *Bioconjugate Chem*. 2001, 12, 476-484, vol. 12, No. 4, Jul./Aug. 2001.

Di Blasio, Benedetto et al., Conformation for a β-cyclodextrin monosubstituted with a cyclic dipeptide, *Proc. Natl. Acad. Sci. USA*, vol. 89, pp. 7218-7221, Aug. 1992.

Watanabe, Junji et al., Prepoaration and characterization of poly(ethylene glocol) hydrogels cross-linked by hydrolyzable polyrotaxane, J. Biomater. Sci. Edn, vol. 11, No. 12, pp. 1333-1345, 2000.

Bibby, David C. et al., Investigation into the structure and composition of β-cyclodextrin/poly(acrylic acid) microspheres, International Journal of Pharmaceutics, 180, 1999 Elsevier Science, pp. 161-168.

Ohmura, Yasushi et al., Self-assembling dendritic supramolecle of molecular nanotubes and starpolymers, *Langmuir* 2000, 16, American Chemical Society, pp. 10278-10280.

B.Mayer, CH.Th.Kleim, I.N.Topchieva & G.Kohler,Selective Assembly of Cyclodextrins on Poly(Ethylene Oxide)-Poly(Propylene Oxide) Block Copolymers, *Journal of Computer-Aided Molecular Designs*, 13: 373-383, 1999.

Suzie J. Hwang, Nathalie C. Bellocq & Mark E. Davis, Effects of Structure of β-Cyclodextrin-Containing Polymers on Gene Delivery, *Division of Chemistry and Chemical Engineering, California Institute of Technology*, Pasadena, California 91125. Received Sep. 8, 2000; Revised Manuscript Received Dec. 21, 2000.

Hector Gonzalez, Sue Jean-Hwang and M.E. Davis, New Class of Polymers for the Delivery of Macromolecular Therapeutics, *Division of Chemistry and Chemical Engineering*, California Institute of Technology, Pasadena, California 91125, Received Jun. 9, 1999; Revised Manuscript Received Aug. 6, 1999. Published on Web Sep. 24, 1999.

Eva Fenyvesi, Osamu Shirakur, Jozsef Szejtli & Tsuncji Nagai, Properties of Cyclodextrin Polymer as a Tabletting Aid, *Chem. Pharm. Bull.* 32(2) 665-669 (1984).

Josef Pitha, S.Mitchel Harman & Mary Ellen Michel, Hydrophilic Cyclodextrin Derivatives Enable Effective Oral Administration of Steroidal Hormones, *Journal of Pharmaceutical Sciences*/vol. 75, No. 2, Feb. 1986.

Marcella Chiari, Viviana Desperatl, Marina Cretich, Gregorio Crini, Ludovic Janus & Michel Morcellet, Vinylpyrrolidine-β-Cyclodextrin Copolymer: A Novel Chiral Selector for Capillary Electrophoresis, *Electrophoresis 1999*, 20, 2614-2618.

Akira Harada, Masaoki Furue & Shun-Ichi Nozakura, Cyclodextrin-Containing Polymers, vol. 9, No. 5, Sep.-Oct. 1976.

K. Uekama, M. Otagiri, T. Irie, H.Seo & M. Tsuruoka, Improvement of Dissolution and Absorption Characteristics of Phenytoin by a Water-Soluble β-Cyclodextrin-Epichlorohydrin Polymer, IJP 00774, Sep. 7, 1984.

Julianna Szeman, Haruhisa Ueda, Jozsef Szeitli, Eva Fenyvesi, Yoshiharu Machida & Tsuneji Nagai, Complexation of Several Drugs with Water-Soluble Cyclodextrin Polymer, *Chem. Pharm. Bull.* 35(1) 282-288 (1987).

Akira Harada, Masaoki Furue & Shun-ichi Nozakura, Inclusion of Aromatic Compounds by a β-Cyclodextrin-Epichlorohydrin Polymer, *Polymer Journal*, vol. 13, No. 8, pp 777-781(1981).

Akira Harada, Masaoki Furue & Shun-ichi Nozakura, Cyclodextrin-Containing Polymers. 2. Cooperative Effects in Catalysis and Binding, vol. 9, No. 5, Sep.-Oct. 1976.

Marcella Chiari, Marina Cretich, Gregorio Crini, Ludovic Janus, Michel Morcellet, Allylamine-β-Cyclodextrin Copolymer, a Novel Chiral Selector for Capillary Electrophoresis, *Journal of Chromatography A*, 894 (2000) 95-103.

K. Matsubara, T. Irie, K. Uekama, Controlled Release of the LHRH Agonist Buserelin Acetate from Injectable Suspensions Containing Triacetylated Cyclodextrins in an Oil Vehicle, *Journal of Controlled Release 31* (1994) 173-180.

Kouzou Miyake, Fumitoshi Hirayama & Kaneto Uekam, Solubility and Mass and Nuclear Magnetic Resonance Spectroscopic Studies on Interaction of Cyclosporin a with Dimethyl-α- and -β-Cyclodextrins in Aqueous Solution, *Journal of Pharmaceutical Sciences*/vol. 88, No. 1, Jan. 1999.

Benito Casu, Mario Reggiani & George R. Sanderson, Methylated Cycloamyloses (Cyclodextrins) and Their Inclusion Properties, Jan. 22, 1979.

Kaneto Uekama, Naoki Hirashima, Yasuhide Horiuchi, Fumitoshi Hirayama, Takanori Ijitsu & Masao Ueno, Ethylated β-Cyclodextrins as Hydrophobic Drug Carriers: Sustained Release of Diltiazem in the Rat, *Journal of Pharmaceutical Sciences* vol. 76, No. 8, Aug. 1987.

Kaneto Uekama, Hidetoshi Arima, Tetsumi Irie, Kazutaka Matsubara & Takeo Kuriki, Sustained Release of Buserelin Acetate, a Luteinizing Hormone-Releasing Hormone Agonist, from an Injectable Oily Preparation Utilizing Ethylated β-Cyclodextrin, *J. Pharm. Pharmacol. 1989*, 41: 874 876 Communicated May 26, 1989.

Teruko Imai, Masaki Otagiri, Hazime Saito & Kaneto Uekama, Inclusion Mode of Flurbiprofen with β-Cyclodextrin and Heptakis(2,3,6-Tri-O-methyl)-β-Cyclodextrin, and Improvements of Some Pharmaceutical Properties of Flurbiprofen by Complexation, *Chem. Pharm. Bull.* 36(1) 354-359 (1988).

Valentino J. Stella & Roger A. Rajewski, Cyclodextrins: Their Future in Drug Formulation and Delivery, *Pharmaceutical Research*, vol. 14, No. 5, 1997.

Dominique Duchene, Denis Wouessidjewe, Gilles Ponchel, Cyclodextrins and Carrier Systems, *Journal of Controlled Release 62* (1999) 263–268.

James Blanchard & Stefan Proniuk, Some Important Considerations in the Use of Cyclodextrins, *Pharmaceutical Research*, vol. 16, No. 12, 1999.

Alan P. Croft & Richard A. Bartsch, Synthesis of Chemically Modified Cyclodextrins, *Tetrahedron vol. 39*, No. 9, pp. 1477 to 1474, 1983, Printed in Great Britain.

Fumitoshi Hirayama, Shiuhei Mieda, Yuji Miyamoto, Hidetoshi Arima & Kaneto Uekama, Heptakis (2,6–di–O–Methyl–3–O–Acetyl)β–Cyclodextrin: A Water–Soluble Cyclodextrin Derivative with Low Hemolytic Activity, *Journal of Pharmaceutical Sciences vol. 88*, No. 10, Oct. 1999.

Roger A. Rajewski, George Traiger, James Bresnahan, Parinaz Jaberaboansari, Valentino J. Stella & Diane O. Thompson, Preliminary Safety Evaluation of Parenterally Administered Sulfoalkyl Ether β–Cyclodextrin Derivatives, *Journal of Pharmaceutical Sciences vol. 84*, No. 8, Aug. 1995.

Xichen Zhang, John K. Jackson, Helen B. Burt, Development of Amphiphilic Diblock Copolymers as Micellar Carriers of Taxol, *International Journal of Pharmaceutics 132* (1996) 195–206.

Richard B. Greenwald, Carl W. Gilbert, Annapuma Pendri, Charles d. Conover, Jing Xia & Anthony Martinez, Drug Delivery Systems: Water Soluble Taxol 2'–Poly(Ethylene Glycol) Ester Prodrugs–Design and in Vivo Effectiveness, *J. Med. Chem 1996*, 39, 424–431.

Suzie J. Hwang, Nathalie C. Bellocq & Mark E. Davis, Effects of Structure of β–Cyclodextrin–Containing Polymers on Gene Delivery, Division of Chemistry and Chemical Engineering, California Institute of Technology, Pasadena, California 91125, Revised Manuscript Received Dec. 21, 2000.

B. Mayer, Ch.Th.Klein, I.N. Topchieva & G. Kohler, Selective Assembly of Cyclodextrins on Poly (Ethylene Oxide)–Poly(Propylene Oxide) Block Copolymers, *Journal of Computer–Aided Molecular Design. 13*: 373–383, 1999.

Caroline M. Spencer & Diana Faulds, A Review of its Pharmacodynamic and Pharmacokinetic Properties and Therapeutic Potential in the Treatment of Cancer, *Drugs 48(5)*: 794–847, 1994.

Cristina Monfardini and Francesco M. Veronese, Stabilization of Substances in Circulation, *Bioconjugate Chem. 1998*. 9, 418–450.

Samuel Zalipsky, Functionalized Poly(Ethylene Glycol) for Preparation of Biologically Relevant Conjugates, *Bioconjugate Chem*. 1995. 6. 150–165.

A. Gabizon & F. Martin, Polyethylene Glycol–Coated (Pegylated) Liposomal Doxorubicin, *Drugs 1997*: 54 Suppl. 4: 15–21, 0012–6667/97/0004–0015/503 50/0.

Marie–Christine Jones & Jean–Christophe Leroux, Polymeric Micelles—A New Generation of Colloidal Drug Carriers, *European Journal of Pharmaceutics and Biopharmaceutics 48* (1999) 101–111.

E. Piskin, X. Kaitian, E.B. Denkbas & Z. Kucukyavuz, Novel PDLLA/Peg Copolymer Micelles as Drug Carriers, *J. Biomater, Sci. Polymer Edn*, vol. 7, No. 4, pp. 359–373 (1995).

Young–II Jeong, Jac–Woon Nah, Hyun–Chul Lee, Sung–Ho Kim & Chong–Su Cho, Adriamycin Release from Flower–Type Polymeric Micelle Based on Star–Block Copolymer Composed of Poly($\gamma$–Benyl L–Glutamate) as the Hydrophobic Part and Poly(Ethylene Oxide) as the Hydrophilic Part, *International Journal of Pharmaceutics 188*(1999) 49–58.

G. Kwon, M. Naito, M. Yokoyama, T. Okano, Y. Sakuria, K. Kataoka, Block Copolymer Micelles for Drug Delivery: Loading and Release of Doxorubicin, *Journal of Controlled Release 48* (1997) 195–201.

Masayuki Yokoyama, Shigeto Fukushima, Ryuji Uehara, Kazuya Okamoto, Kazunori Kataoka, Yasuhisa Sakurai & Teruo Okano, Characterization of Physical Entrapment and Chemical Conjugation of Adriamycin in Polymeric Micelles and their Design for in vivo Delivery to a Solid Tumor, *Journal of Controlled Release 50* (1998) 79–92.

Kazunori Kataoka, Tsuyoshi Matsumoto, Masayuki Yokoyama, Teruo Okano, Yasuhisa Sakurai, Shigeto Fukushima, Kanuya Okamoto & Glen S. Kwon, Doxorubicin–Loaded Poly(Ethylene Glycol)–Poly (β–Benzyl–L–Aspartate) Copolymer Micelles: their Pharmaceutical Characteristics and Biological Significance, *Journal of Controlled Release 64* (2000) 143–153.

Uma S. Sharma, Sathyamangalam V. Balasubramanion & Robert M. Staubinger, Pharmaceutical and Physical Properties of Paclitaxel (Taxol†) Complexes with Cyclodextrins‡, Journal of Pharmaceutical Sciences vol. 84, No. 10, Oct. 1995.

Chun Li, Dongfang Yu, Tomio Inoue, David J. Yang, Luka Milas, Nancy r. Hunter, E. Edmund Kim & Sidney Wallace, Synthesis and Evaluation of Water–Soluble Polyethylene Glycol–Paclitaxel Conjugate as a Paclitaxel Prodrug, *Anti–Cancer Drugs 1996*. 7. pp. 642–648.

Michal Pechar, Karel Ulbrich & Vladimir Subr, Poly(Ethylene Glycol)Multiblock Copolymer as a Carrier of Anti–Cancer Drug Doxorubicin, *Bioconjugate Chem.*. vol. 11, No. 2, 2000.

Jean–Francois Pons, Jean–Luc Fauchere, Frederic Lamaty, Annie Molla & Rene Lazaro, A Constrained Diketopiperazine as a New Scaffold for the Synthesis of Peptidomimetics, *Eur.J.Org.Chem*. 1998, 853–859.

Feng Liu, Soo Chang Song, Don Mix, Miroslav Baudys & Sung Wan Kim, Glucose–Induced Release of Glycosylpoly(Ethylene Glycol) Insulin Bound to a Soluble Conjugate of Concanavalin A, *Bioconjugate Chem*. 1997, 8, 664–672.

Kwon et al, Enhanced Tumor Accumulation and Prolonged Circulation Times of Micelle–forming poly(ethylene oxide–aspartate) Block Copolymer–adriamycin Conjugates, *J. Control Rel*. 29, 17–23 (1994).

Helmlinger G, Yuan F, Dellian M, Jain R.K.—Interstitial pH and p02 Gradients in Solid Tumors—*Nat Med*. Feb. 1997;3(2):177–82.

Duncan R—Drug–polymer Conjugates: potential for Improved ch—*Anticancer Drugs*. Jun. 1992;3(3):175–210.

Hirayama F; Mieda S; Miyamoto Y; Arima H; Uekama K—Heptakis(2, 6–di–0–methyl–3–0–acetyl)–beta–cylodex—*J Pharm Sci*. Oct. 1999; 88(10):970–5.

Sharma A; Mayhew E; Bolesak L; Cavanaugh C; Harmon P; Janoff A; Bernacki RJ—Activity of Paclitaxel Liposome Formulations again—*Int J Cancer*, Mar. 28, 1997;71(1);103–7.

Rajewski RA; Traiger G; Bresnahan J; Jaberaboansari P; Stella VJ; Thompson DO—Preliminary Safety Evaluation of Parenterally Admi—*J Pharm Sci*. Aug. 1995;84(8):927–32.

Tannock IF; Rotin D—Acid Ph in Tumors and its potential for Therapeutic—*Cancer Res*. Aug. 15, 1989;49(16):4373–84.

Sharma US; Balasubramanian SV; Straubinger RM—Pharmaceutical and Physical Properties of Paclitax—*J Pharm Sci*. Oct. 1995;84(10):1223–30.

Takakura Y; Hashida M—Macromolecular Drug Carrier Systems in Cancer Chem—*Crit Rev Oncol Hematol*. Mar. 1995;18(3):207–31.

Greenwald RB; Conover CD; Choe YH—Poly(ethylene glycol) conjugated Drugs and Prodrug—*Crit Rev Ther Drug Carrier Syst*. 2000;17(2):101–61.

Litzinger DC; Huang L.—Phosphatidylethanolamine Liposomes: drug Delivery—*Biochim Biophys Acta*. Aug. 1992 14;1113(2):201–27.

Supplementary European Search Report for corresponding EP application No. 02795700.0.

Huh et al., Synthesis of alpha–Cyclodextrin–Conjugated Poly(epsilon–lysine)s and Their Inclusion Complexation Behavior, *Marcromol. Rapid Commun.*, 2002, 23:3, 179–182.

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: biodegradable peptide linker

<400> SEQUENCE: 1

Gly Phe Leu Gly
1

CYCLODEXTRIN GRAFTED BIOCOMPATIBLE AMPHILPHILIC POLYMER AND METHODS OF PREPARATION AND USE THEREOF

BACKGROUND OF THE INVENTION

This invention relates to novel polymeric bioactive agent carriers. More particularly, the invention relates to cyclodextrin-grafted biocompatible polymers used as bioactive agent carriers and methods of making thereof.

Many biologically active molecules such as anti-viral agents, anti-cancer agents, peptides/proteins and DNA, effective for a variety of therapeutic applications, have become commercially available through advances in recombinant DNA and other technologies. However, an ideal carrier for drugs and active agents is always needed to facilitate their solubility, delivery and effectiveness.

Cyclodextrins (CDs) are cyclic oligosaccharides, usually consisting of six to eight glucose units, which have a truncated cone shape with the wide open side being formed by secondary hydroxyl groups (2-OHs and 3-OHs) and the narrower side by primary hydroxyl groups (6-OHs). Cyclodextrins provide for unique micro-heterogenous environments since the exterior of the molecule is hydrophilic while the cavity is hydrophobic due to the relatively high electron density. The inclusion properties of cyclodextrins, namely, complex-formation between a guest molecule and a cyclodextrin molecule, have been extensively investigated. The complexes, which are formed in the solid state and in solution, consist of guest molecules which are held in the cavity of the host cyclodextrin and are stabilized by Van der Waals forces, and, to a lesser extent, by dipole-dipole interactions. Inclusion complexes in aqueous solutions are thought to be further stabilized by hydrophobic interactions, i.e., by the tendency of solvent water to push hydrophobic solutes of suitable size and shape into the essentially hydrophobic cavity, in order to attain the "most probable structure" of the solvent and obtain minimal energy in the overall system.

Practical use of natural cyclodextrins ($\alpha$-, $\beta$-, and $\gamma$-CDs) as drug carriers is restricted by their low aqueous solubility. Safety is another major concern of cyclodextrins being used as drug carriers due to the toxicity of CD. Modification of the parent cyclodextrin to improve safety while maintaining the ability to form inclusion complexes with various substrates has been the goal of numerous research groups. Some groups have also focused on improving interaction between the pharmaceuticals and the cyclodextrins while others have attempted to prepare materials that can be chemically defined more precisely.

The two most promising cyclodextrin derivatives which are suitable for parenteral administration are hydoxylpropyl $\beta$-cyclodextrin (HP$\beta$CD or HPCD) and sulfobutylether-$\beta$-cyclodextrin (SBE$\beta$CD or SBE-CD). HP$\beta$CD has generally been found to be safe when administered parenterally in animals and humans [Pitha et al, *J Pharm Sci,* 84 (8), 927–32 (1995)]. Minor reversible histological changes have been observed in high dose animal studies (100–400 mg/kg) and more significant hematological changes were observed in these high dose studies suggesting red blood cell damage had occurred. No adverse effects were observed in human studies. SBE$\beta$CD has also been found to be safe when administered parenterally in mice [Rajewski et al, *J Pharm Sci,* 84 (8), 927–32 (1995)]. However, like most of the modified cyclodextrins, the binding constant between drugs and HP$\beta$CDs is usually less than those with the parent or unmodified cyclodextrin. Due to steric hindrance of the host molecule, the higher the degree of hydroxylpropyl substitution the poorer the drug binding.

Hydrophobic modifications of cyclodextrins have also been prepared in attempts to improve the formulations of some CD inclusionable drugs. It was found that partial methylation of the hydroxyl groups at the 2- and 6-position of $\beta$-cyclodextrin (DM-$\beta$CD or DMCD) generally leads to stronger drug binding due to increased hydrophobic interactions. Although the methylated cyclodextrins are highly water soluble, they also have greater toxicity. The toxicity of DM$\beta$CD was reduced significantly by modifying the free 3-hydroxyl groups with acetyl groups. This indicates that water-soluble cyclodextrin derivatives with superior bio-adaptability and inclusion ability can be prepared by carefully selecting the substitution groups. Controlling the degree of substitution is also important in balancing water solubility and complexing capability. When the substitution groups are more hydrophobic than methyl groups, such as an ethyl group, an acetyl group, etc., the whole cyclodextrin derivative becomes practically water insoluble. These compounds have been shown to have potential application as sustained release carriers for water-soluble drugs. Among the alkylated cyclodextrins, heptakis(2,6-di-O-ethyl)-$\beta$-cyclodextrin and heptakis(2,3,6-tri-ethy)-$\beta$-cyclodextrin were the first slow-release carriers to be used in conjunction with water soluble diltiazem, isosorbide dinitrate, and the peptide buserelin acetate.

On the other hand, the peracylated cyclodextrins with medium alkyl chain lengths ($C_4$–$C_5$) are particularly useful as novel hydrophobic carriers due to their multifunctional and bioadaptable properties. They have broad applicability for various routes of administration: for example, the bio-adhesive properties of heptakis(2,3,6-tri-O-butanoyl-$\beta$-cyclodextrin ($C_4$) can be used in oral and transmucosal formulations, while the film-forming properties of heptakis (2,3,6-tri-O-valeryl)-$\beta$-cyclodextrin ($C_5$) are useful in transdermal preparations. In oral applications, the release of molsidomine, a water-soluble and short-half life drug, was markedly retarded by complexation with peracylated-$\beta$-cyclodextrins in decreasing order of their solubility, particularly by those having carbon chains longer than the butylated derivatives. When the complexes were administered orally to beagle dogs, heptakis(2,3,6-tri-O-butanoyl)-$\beta$-cyclodextrin suppressed the peak plasma level of molsidomine and maintained a sufficient drug level for a long period, while use of other derivatives having shorter or longer chains than heptakis(2,3,6-tri-O-butanoyl)-$\beta$-cyclodextrin proved to be insufficient. This indicates that heptakis(2,3,6-tri-O-butanoyl)-$\beta$-cyclodextrin may be a useful carrier for orally administered water-soluble drugs, especially for drugs which are metabolized in the GI tract. The superior and sustained effect exhibited with the heptakis (2,3,6-tri-O-butanoyl)-$\beta$-cyclodextrin may be a result of both increased hydrophobicity and mucoadhesive properties. Because of its hydrophobicity, heptakis(2,3,6-tri-O-butanoyl)-$\beta$-cyclodextrin, as well as other hydrophobic cyclodextrin derivatives, can only be used in solid or oily formulations. On the other hand, like natural $\beta$-cyclodextrin, their membrane toxicity, which causes tissue irritation and hemolysis in a concentration-dependent manner is another limitation of their pharmaceutical application. For example, the concentration of DM-$\beta$-CD that induces 50% hemolysis of human erythrocytes is lower than that of so called bioadaptable CD derivatives such as 2-hydroxypropyl-$\beta$-CD, sulfobutyl ether of $\beta$-CD, and maltosyl-$\beta$-CD. The hemolytic activity of cyclodextrins is associated with the extraction of membrane components, mainly through inclusion action with cholesterol. However, this drawback can be overcome by further structural modification of alkylated CDs, for example, heptakis (2,6-di-O-methyl-3-O-acetyl)-β-CD (DMA-β-CD) was found to have much weaker hemolytic activity while keeping a similar inclusion ability to that of DM-β-CD [Hirayama et al, *J Pharm Sci*, 88 (10), 970–5 (1999)]. Since cyclodextrins are poorly adsorbed from the GI tract following oral administration, the oral administration of cyclodextrins raises minimal safety concerns that may result from the systemic absorption of the cyclodextrins themselves. However, cyclodextrins may cause secondary systemic effects through increased GI elimination of certain nutrients and bile acids. This effect is most notable for γ-cyclodextrin assisted fecal elimination of bile acids. The increased elimination, however, was only observed at very high oral doses of cyclodextrin (up to 20% of diet). The secondary effects of the increased bile acid elimination are increased conversion of serum cholesterol to the bile acids with subsequent lowering of plasma cholesterol levels.

For years, various kinds of cyclodextrins have been prepared to improve the physicochemical properties and inclusion capabilities of parent cyclodextrins, and some of the pharmaceutical products containing cyclodextrins have been approved. Because large amounts of cyclodextrins are necessary to alter the solubility properties of the drugs being carried, the toxicity of the cyclodextrin needs to be very low in order to safely delivery the necessary dose of a drug. Therefore either reducing the total dose or reducing the intrinsic toxicity of cyclodextrins can widen the pharmaceutical applications of cyclodextrins.

In view of the foregoing, it will be appreciated that providing improved cyclodextrin containing bioactive agent carriers and a method of using them would be a significant advancement in the art.

BRIEF SUMMARY OF THE INVENTION

The present invention provides a new class of amphiphilic cyclodextrin containing polymers wherein multiple hydrophobic cyclodextrin or derivitized cyclodextrin moieties are conjugated with or grafted to a biocompatible hydrophilic polymeric backbone, through appropriate biodegradable or non-biodegradable linkers. Optionally, one or more or a mixture of targeting moieties (TM) may also be covalently bound to the polymeric backbone. The CD-grafted polymers of the present invention can be synthesized by coupling two to thirty CDs or derivatives thereof to a hydrophilic polymer, i.e. a polyethylene glycol (PEG) or poly N-(2-hydroxylpropyl)methacrylamide) (HPMA), via a proper linker. If desired, as described above, one or more targeting moieties(TM) may optionally be covalently attached to the polymer backbone. The purpose of using the targeting moiety is to target particular cells for drug delivery. The synthesized carrier, namely a hydrophobic CD-grafted hydrophilic polymer, results in better solubility and reduced cytotoxicity of the drug/carrier complex.

DETAILED DESCRIPTION OF THE INVENTION

Figure 1:
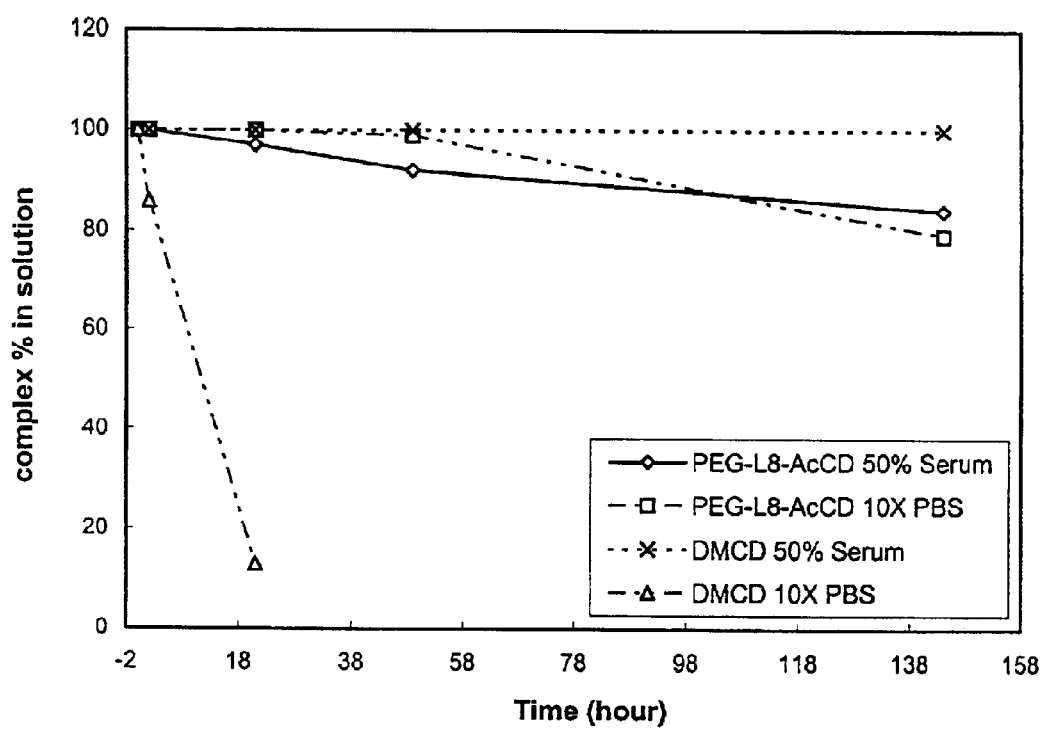
FIG. 1 is a graphic illustration showing the stability of Paclitaxel/CD complexes in 50% serum or 10×PBS dilutions.
Figure 2:
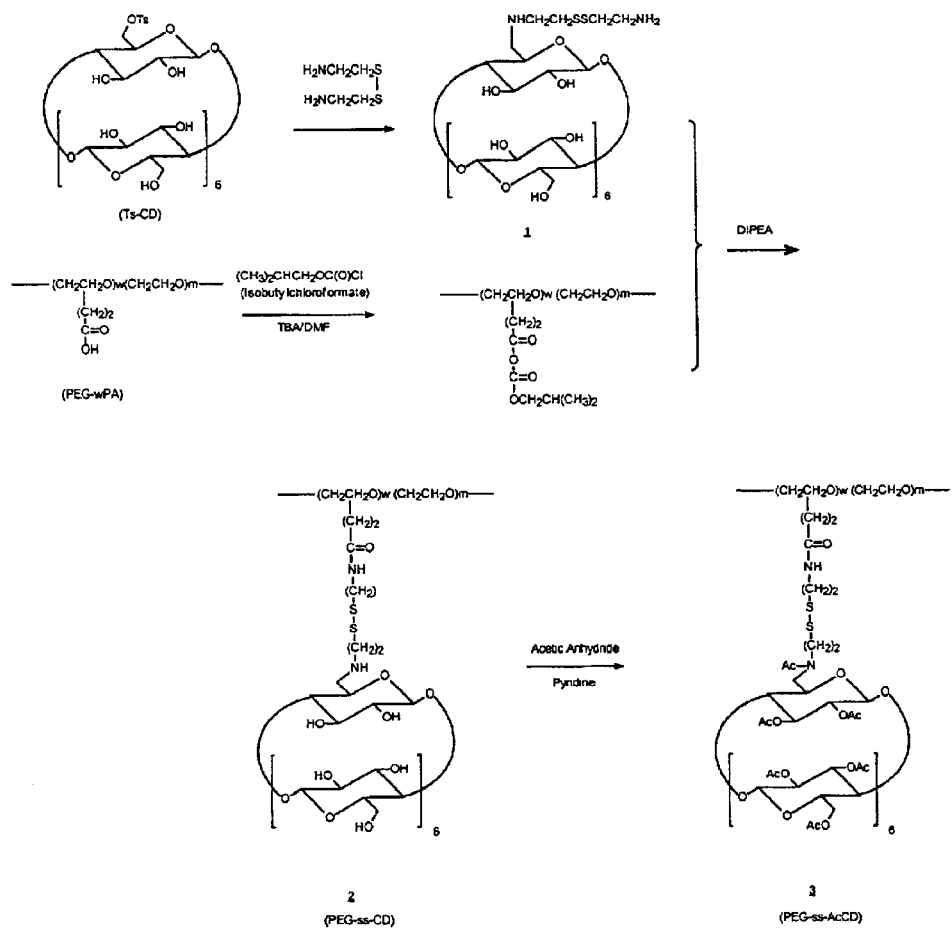
FIG. 2 depicts a reaction scheme for synthesis of PEG-SS-AcCD
Figure 3:
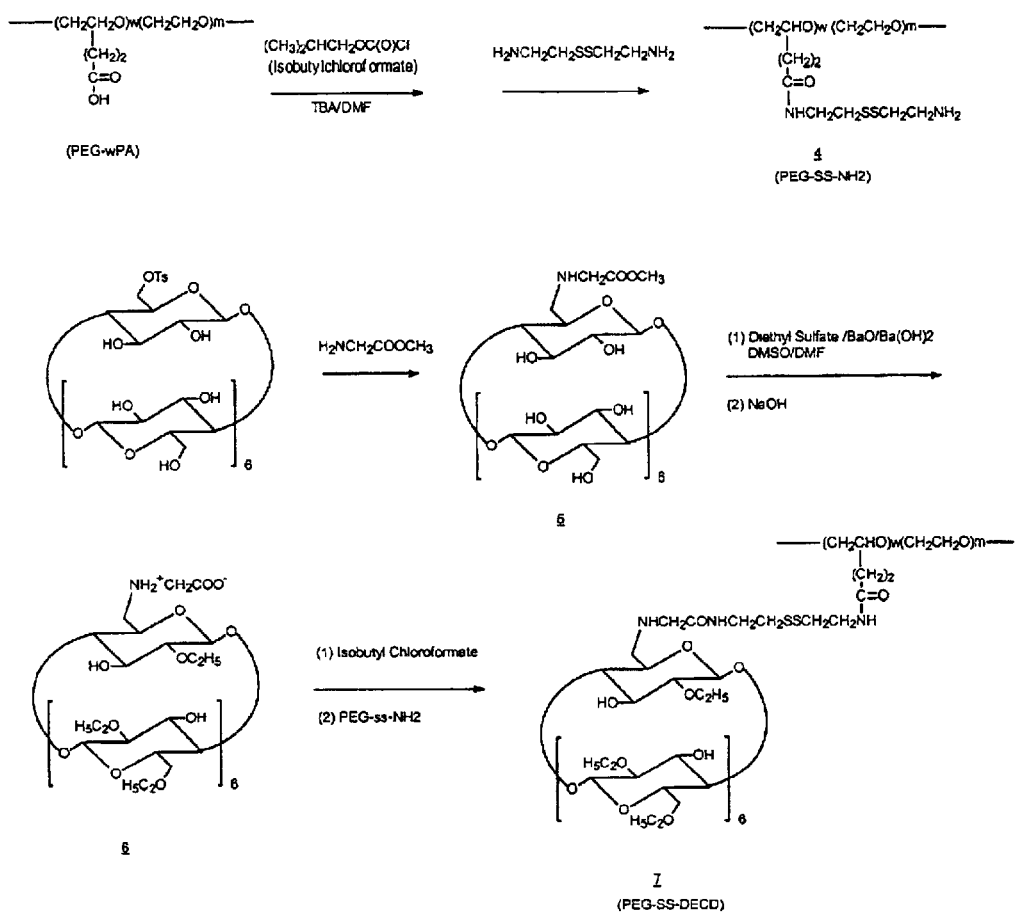
FIG. 3 depicts a reaction scheme for synthesis of PEG-SS-DECD.

Before the present composition and method for drug delivery are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

"Active agents" refers to those agents that can function as guest molecules of the instant invention. Active agents include chemicals and other substances which can form an inclusion complex with a cyclodextrin or derivatized cyclodextrin grafted polymer and are inhibitory, antimetabolic or preventive toward any disease (i.e. cancer, syphilis, gonorrhea, influenza and heart disease) or inhibitory or toxic toward any disease causing agent. Active agents include numerous drugs such as anticancer drugs, antineoplastic drugs, antifungal drugs, antibacterial drugs, antiviral drugs, cardiac drugs, neurological drugs, and drugs of abuse; alkaloids (i.e. camptothecins), antibiotics, bioactive peptides, steroids, steroid hormones, polypeptide hormones, interferons, interleukins, narcotics, nucleic acids including antisense oligonucleotides, pesticides and prostaglandins. Active agents also include aflatoxins, ricins, bungarotoxins, irinotecan, ganciclovir, furosemide, indomethacin, chlorpromazine, methotrexate, cevine derivatives and analogs including cevadines, desatrines, veratridine. It also includes various flavone derivatives and analogs including dihydroxyflavones (chrysins), trihydroxyflavones (apigenins), pentahydroxyflavones (morins), hexahydroxyflavones (myricetins), flavyliums, quercetins, fisetins; various antibiotics including penicillin derivatives (i.e. ampicillin), anthracyclines (i.e. doxorubicin, daunorubicin), teramycins, tetracyclines, chlorotetracyclines, clomocyclines, butoconazole, ellipticines, guamecyclines, macrolides (i.e. amphotericins), filipins, fungichromins, nystatins; various purine and pyrimidine derivatives and analogs including 5'-fluorouracil, 5'-fluoro-2'-deoxyuridine, and allopurinol; various photosensitizer substances, especially those used for singlet and triplet oxygen formation useful for photodynamic, phthalocyanine, porphyrins and their derivatives and analogs; various steroid derivatives and analogs including cholesterols, digoxigenins; various coumarin derivatives and analogs including dihydroxycoumarins (esculetins), dicumarols; chrysarobins, chrysophanic acids, emodins, secalonic acids; various dopas, derivatives and analogs including dopas, dopamines, epinephrines, and norepinephrines (arterenols).

"Parenteral" shall mean intramuscular, intraperitoneal, intra-abdominal, subcutaneous, and, to the extent feasible, intravenous and intraarterial.

"Biocompatible" means that the substance is nonimmunogenic, nonallergenic and will cause minimum undesired physiological reaction. They may be degraded biologically and they are "biologically neutral" in that they lack specific binding properties or biorecognition properties.

"Linkers" or "linkages" are defined as types of specific chemical moieties or groups used within the chemical substances that covalently couple the cyclodextrin moiety to the polymer backbone and may be either biodegradable or non-biodegradable. Suitable linkers are more specifically defined below.

"Drug" shall mean any organic or inorganic compound or substance having bioactivity and adapted or used for a therapeutic purpose. Proteins, hormones, anti-cancer agents, oligonucleotides, DNA, RNA and gene therapies are included under the broader definition of drug.

"Peptide," "polypeptide," "oligopeptide" and "protein" shall be used interchangeably when referring to peptide or protein drugs and shall not be limited as to any particular molecular weight, peptide sequence or length, field of bioactivity or therapeutic use unless specifically stated.

"Targeting moiety" refers to those moieties that bind to a specific biological substance or site. The biological substance or site is considered the "target" of the targeting moiety that binds to it. Examples of suitable targeting moieties are described below. Examples of suitable targeting moieties includes antigens, haptens, biotin, biotin derivatives, lectins, galactosamine and fucosylamine moieties, receptors, substrates, coenzymes, cofactors, proteins, histones, hormones, vitamins, steroids, prostaglandins, synthetic or natural polypeptides, carbohydrates, lipids, antibiotics, drugs, digoxins, pesticides, narcotics, neuro-transmitters, and various nucleic acids.

A "nucleic acid" is defined as any nucleic acid sequence from any source. The nucleic acid includes all types of RNA, DNA, and oligonucleotides including probes and primers used in polymerase chain reaction (PCR) or DNA sequencing, antisense oligonucleotides and phosphorthioate oligonucleotides. Also included are synthetic nucleic acid polymers, such as methylphosphonate oligonucleotides, phosphotriester oligonucleotides, mopholino-DNA and peptide nucleic acids (PNA) including PNA clamps, DNA and/or RNA fragments, and derivatives from any tissues, cells, nuclei, chromosomes, cytoplasm, mitochondria, ribosomes, and other cellular sources.

A "cyclodextrin (CD)", is a cyclic oligosaccharide composed of glucose monomers coupled together to form a conical, hollow molecule with a hydrophobic interior or cavity. The cyclodextrins of the instant invention can be any suitable cyclodextrin, including alpha-, beta-, and gamma-cyclodextrins, and their combinations, analogs, isomers, and derivatives. Cyclodextrins can be either natural or modified with hydrophobic groups as will be described in greater detail below.

In describing this invention, references to a cyclodextrin "complex", means a noncovalent inclusion complex. An inclusion complex is defined herein as a cyclodextrin or derivatized cyclodextrin functioning as a "host" molecule, combined with one or more "guest" molecules that are contained or bound, wholly or partially, within the hydrophobic cavity of the cyclodextrin or its derivative. Most preferred CDs are derivatives such as carboxymethyl CD, glucosyl CD, maltosyl CD, hydroxypropyl cyclodextrins (HPCD), 2-hydroxypropyl cyclodextrins, 2,3-dihydroxypropyl cyclodextrins (DHPCD), sulfobutylether CD, acylated, ethylated and methylated cyclodextrins. Also preferred are oxidized cyclodextrins that provide aldehydes and any oxidized forms of any derivatives that provide aldehydes. Also included are altered forms, such as crown ether-like compounds and higher homologues of cyclodextrins.

"Controlled release" is defined as the release of a captured guest molecule/drug from the CD polymer carrier only by cleavage of certain linkages that were used to synthesize the carrier.

This invention relates to novel CD-grafted biocompatible amphiphilic polymers and the methods of preparation thereof for use as bioactive agent carriers. The invention, in one of its most general definitions, concerns a complex between a bioactive agent and at least one CD-grafted polymeric conjugate comprising a biocompatible hydrophilic polymer backbone such as PEG and HPMA, poly-L-Lysine (PLL) and polyethylenimine (PEI) which is grafted with at least one, and preferably a multiplicity, of hydrophobically modified CDs. Optionally a targeting moiety (TM) may be covalently linked to the polymeric carrier.

The preferred cyclodextrin containing polymers may be defined by a cyclodextrin containing polymer wherein cyclodextrin or derivatized cyclodextrin moieties are connected to a biocompatible hydrophilic polymer backbone by a single spacer arm to the 2, 3, or 6-position of the cyclodextrin which can be represented by Formula 1 as follows:

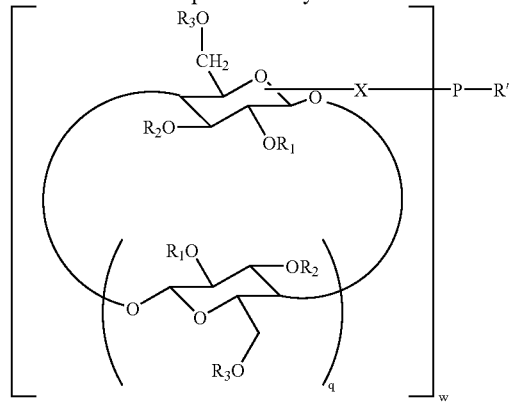

(1) P is a biocompatible hydrophilic polymer backbone having a molecular weight range from 2,000 to 1,000,000 Daltons, preferably 5,000 to 70,000 Daltons, and most preferably 20,000 to 40,000 Daltons. Preferably the biocompatible polymer backbone is a hydrophilic polymer selected from the group consisting of polyethylene glycol (PEG), N-(2-hydroxypropyl)methacrylamide polymer (HPMA), polyethylenimine (PEI) and polylysine (pLL) which are appropriately endcapped as is known in the prior art and which also may be substituted with substituents that do not adversely affect the functionality of the polymer for its intended purpose. Preferably biocompatible polymer backbone is a polyethylene glycol (PEG) polymer. When the cyclodextrin is attached at the 2, 3 or 6 position of the cyclodextrin the corresponding $R_1O-$, $R_2O-$ or $R_3O-$ group will be replaced and the 2-, 3- or 6-carbon of the glucopyranose will be covalently attached to linker X;

(2) R' is a member selected from the group consisting of hydrogen, a tissue targeting moiety (TM) or a cell membrane fusion moiety (FM) as described herein with the proviso that a mixture of hydrogen, targeting moieties and cell fusion moieties may be found on the same polymer backbone and/or within the polymer composition;

(3) X is a linker having the formula:

-Q-Z-Q'- where Q is covalently bonded to the hydrophilic polymer chain either directly or by means of a pendant alkyl or other functional group and Q' is covalently bonded to the cyclodextrin. Q and Q' are independently members selected from the group consisting of $NR_4$, S, O, CO, CONH, and COO. In other words Q and Q' can comprise amine, alkylamine, acylamine, thio, ether, carbonyl, amide or ester moieties. Z comprises a member selected from the group consisting of an alkylene disulfide, $[-(CH_2)_aS-S(CH_2)_a-]$, alkylene $[-(CH_2)_a-]$, alkylene oxide $(-[(CH_2)_aO]_b(CH_2)_a-)$, or a short chained peptide where a is an integer of 1 to 10 and b is an integer of 1 to 20. Preferably Q is an amide and Q' is an amine, alkyl amine or acyl amine and the linker has the formula: $-CONH-Z-NR_4-$. Most preferably Q will be attached to a derivatized polymer chain through an alkylene $(-CH_2-)_a$ group. When Z is an alkylene disulfide, alkylene oxide or peptide, the linker is biodegradable. When Z is alkylene, the linker is non-biodegradable;

(4) $R_1$, $R_2$, $R_3$ and $R_4$ are independently members selected from the group consisting of H, alkyl ($C_{n'}H_{2n'+1}$), alkenyl ($C_{n'+1}H_{2(n'+1)-1}$) or acyl ($C_{n'}H_{2n'+1}CO$) wherein n' is an integer of 1 to 16, preferably 1 to 8, most preferably 1 to 4. When $R_1$, $R_2$, $R_3$ and $R_4$ are H, the cyclodextrin is more hydrophilic in nature. When one or more of $R_1$, $R_2$, $R_3$ and $R_4$ are alkyl, alkenyl or acyl groups, the derivatized cyclodextrin becomes more hydrophobic in nature. Therefore, when each of $R_1$, $R_2$, $R_3$ and $R_4$ is alkyl, alkenyl or acyl, the cyclodextrin is most hydrophobic. The acyl derivatized cyclodextrins are more biodegradable than the alkyl or alkenyl derivatized cyclodextrins;

(5) q is an integer of 5, 6 or 7, which makes the pendant cyclodextrin moiety to be α-, β-, or γ-cyclodextrin derivative, respectively. Preferably q is 6 or 7, and most preferably q is 6. In other words, the preferred cyclodextrin is a β-cyclodextrin;

(6) w is an integer such that each polymer backbone contains between 1.5 and 30 and preferably between 2 and 15 cyclodextrin moieties per 20 KD of polymer backbone. The integer "w" represents an average of cyclodextrin moieties in a polymeric composition since a polymeric composition is a mixture of polymer chains where each polymer in the chain may be variable in length, molecular weight and number of cyclodextrin moieties. Hence, each polymer has a weight average molecular weight and an average number of cyclodextrin moieties per 20 KD of polymer backbone within such polymeric composition.

One embodiment of the present invention is a new class of CD-grafted-biocompatible polyethylene glycol (PEG) polymer which can be represented by Formula 2 as follows:

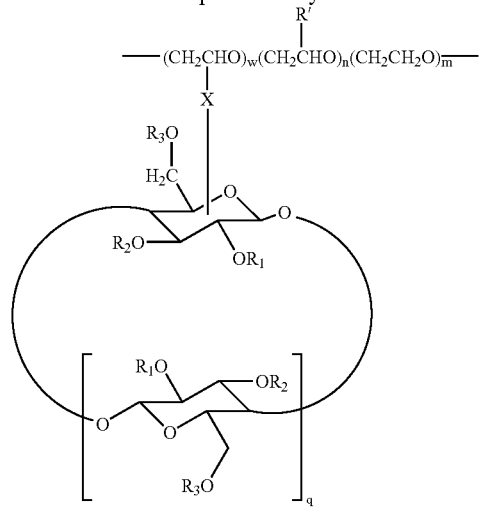

where q, w, X, R, $R_1$, $R_2$, $R_3$ and $R_4$ are as described in Formula 1, m and n are integers sufficient that when combined with w they represent a polyethylene oxide polymeric chain having the molecular weight as described for the hydrophilic polymer in Formula 1. In other words, as noted in Formula 1, the molecular weight of the biocompatible polyethylene oxide hydrophilic polymer backbone is preferably within the range of 5,000 to 1,000,000, more preferably within the range of 5,000 to 70,000 and most preferably within a range of 20,000 to 40,000. As noted in reference to Formula 1, the CDs can be grafted to the polymer by a single arm linker X via the 2, 3 or 6 positions of the CD molecule and, preferably, are grafted via 6 position of the CD molecule. While w has the same numerical value as in Formula 1 it is to be noted that w is used to denote the number of cyclodextrin units per 20K of polymer backbone and does not refer to a polymeric unit containing "w" consecutively joined polyethylene glycol ($CH_2CHXO$) monomers. In other words, the polymer backbone contains "w" monomer units containing a pendent cyclodextrin which are spaced along the polymer backbone. The spacing may be random or uniform depending upon the synthesis.

Most preferably, the cyclodextrin containing polymers, are polyethylene glycol polymer backbones containing pendant CDs having following Formula 3 as follows:

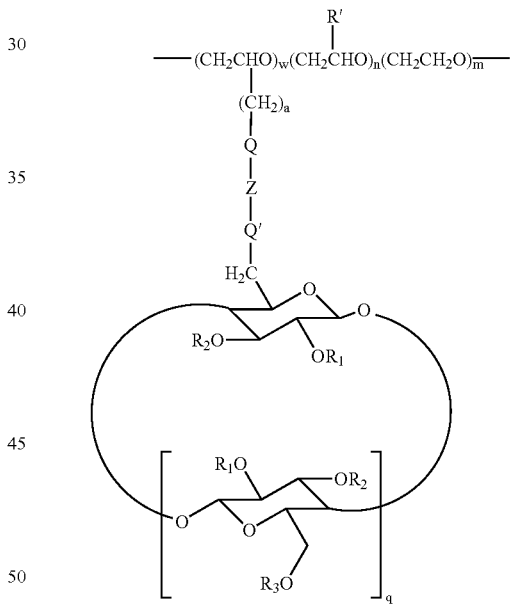

where Q, Q', Z, R, $R_1$, $R_2$, $R_3$, $R_4$, a and q are as described in Formula 1, w is an integer such as to provide between 1.5 and 30 cyclodextrin units, and preferably between 2 and 15 cyclodextrin units per 20 KD polymer chain, as an average, m and n is integers sufficient that when combined with w they represent a polyethylene oxide polymeric chain having the molecular weight as described for the hydrophilic polymer in Formula 1. As explained for Formula 2, the monomeric polyethylene glycol units containing the pendent cyclodextrin are not consecutively joined and may be randomly or uniformly spaced along the polymer backbone.

Specific β-cyclodextrin co-polymers falling within the scope of Formula 3 are listed in Table 1.

TABLE 1

| Comp. No. | CD Polymer ID | w | Q | Z | Q' | $R_1$ | $R_2$ | $R_3$ | $R_4$ |
|---|---|---|---|---|---|---|---|---|---|
| 6 | PEG-SS-CD | 5 | C(O)NH | SS | $NR_4$ | H | H | H | H |
| 13 | PEG-C3-CD | 4.5 | C(O)NH | C3 | $NR_4$ | H | H | H | H |
| 18 (a) | PEG-L8-CD | 5.5 | C(O)NH | L8 | $NR_4$ | H | H | H | H |
| 18 (b) | | 8.5 | | | | | | | |
| 7 | PEG-SS-DECD | 1.5 | C(O)NH | SS | $NR_4$ | $C_2H_5$ | H | $C_2H_5$ | $C_2H_5$ |
| 11 | PEG-GFLG-DECD | 4.5 | C(O)NH | GFLG | $NR_4$ | $C_2H_5$ | H | $C_2H_5$ | $C_2H_5$ |
| 14 | PEG-C3-DECD | 2.6 | C(O)NH | C3 | $NR_4$ | $C_2H_5$ | H | $C_2H_5$ | $C_2H_5$ |
| 20 | PEG-L8-DECD | 3.9 | C(O)NH | L8 | $NR_4$ | $C_2H_5$ | H | $C_2H_5$ | $C_2H_5$ |
| 3 | PEG-SS-AcCD | 5 | C(O)NH | SS | $NR_4$ | $CH_3CO$ | $CH_3CO$ | $CH_3CO$ | $CH_3CO$ |
| 15 | PEG-C3-AcCD | 4.5 | C(O)NH | C3 | $NR_4$ | $CH_3CO$ | $CH_3CO$ | $CH_3CO$ | $CH_3CO$ |
| 19 (a) | PEG-L8-AcCD | 5.5 | C(O)NH | L8 | $NR_4$ | $CH_3CO$ | $CH_3CO$ | $CH_3CO$ | $CH_3CO$ |
| 19 (b) | | 8.5 | | | | | | | |
| 16 | PEG-C3-BnCD | 4.5 | C(O)NH | C3 | $NR_4$ | $C_3H_7CO$ | $C_3H_7CO$ | $C_3H_7CO$ | $C_3H_7CO$ |

In Table 1 SS is —$CH_2CH_2SSCH_2CH_2$—, C3 is —$CH_2CH_2CH_2$—, L8 is —$CH_2CH_2OCH_2CH_2OCH_2CH_2$— and GFLG (SEQ ID NO:1) is the tetrapeptide Gly-Phe-Leu-Gly (SEQ ID NO:1).

These novel CD-grafted polymers of the present invention have the following advantages over their monomer precursors as drug carriers.

First, they have increased water solubility and reduced toxicity. Polyethylene glycol (PEG) is a linear polyether diol with many useful properties, such as good solubility, biocompatibility due to minimal toxicity, immunogenicity, and antigenicity, and good excretion kinetics. These features have made PEG the most extensively studied drug carrier in pharmaceutical research which eventually lead to its FDA approval for internal administration. Therefore PEG can change the physical-chemical properties and toxicities of conjugated cyclodextrins to make them more biocompatible.

In addition, these CD-grafted polymers also provide enhanced guest molecule binding stability. Hydrophobic modification of CDs provides for a more hydrophobic interior and exterior of the cyclodextrin cavity and so increases the stability of inclusion complexes. Moreover multiple CDs in one polymer backbone will increase local CD concentration and produce cooperation in drug binding. Therefore, an amphiphilic co-polymer may form a polymeric micelle after binding to appropriate guest drugs through extra hydrophobic interactions or ionic interactions. Furthermore, these drugs containing CD-grafted polymers can be absorbed by cells through pinocytosis rather than by passive diffusion.

Moreover, the CD-grafted polymer can be used for the controlled-release and targeted-delivery of a bioactive agent. The polymer is likely to form a special type of polymeric micelles with appropriate drugs. Passive drug targeting can increase drug efficiency by targeting specific cells or organs, therefore reducing accumulation of the drug in healthy tissues and minimizing its toxicity thereby allowing higher doses to be administered, if needed. Following intravenous administration, polymeric micelles have been found to have a prolonged systemic circulation time due to their small size and hydrophilic shell, which minimizes uptake by the mononuclear phagocyte system (MPS), and to their high molecular weight which prevents renal excretion. Polymeric micelle-incorporated drugs may accumulate in tumors to a greater extent than the free drug and show reduced distribution into non-targeted areas such as the heart [Kwon et al, *J Control Rel*, 29, 17–23 (1994)]. Accumulation of polymeric micelles in malignant or inflamed tissues may be due to increased vascular permeability and impaired lymphatic drainage (enhanced permeability and retention (EPR) effect. The EPR effect is considered as a passive targeting method, but drug targeting could be further increased by binding to targeting moieties such as antibodies or sugars or by introducing a polymer sensitive to variation in temperature or pH. Targeting micelles or pH sensitive micelles can serve for the delivery of drug to tumors, inflamed tissues or endosomal compartments, since they all are associated with a lower pH than normal tissue [Litzinger et al, *Biochim Biophys Acta*, 1113 (2), 201–27 (1992); Tannock et al, *Cancer Research*, 49 (16), 4373–84 (1989); Helmlinger et al, *Nat Med* 3 (2), 177–82 (1997)].

PEG is commercially available in a variety of molecular masses at low dispersity (Mw/Mn<1.1). Based on their molecular size, they are arbitrarily classified into low molecular weight PEG (Mw<20,000) and high molecular weight PEG (Mw>20,000). Most recent applications of PEG are focused on the attachment of cytotoxic anticancer drugs to the PEG or the grafting of PEG to proteins, micelles or liposomes which leads to a reduction in systemic toxicity, longer retention time within the body, alteration in biological distribution, and improvements in therapeutic efficacy [Takakura et al, Crit Rev Oncol, Hematol 18(3), 207–31 (1995); Duncan et al, *Anticancer Drugs*, 3 (3), 175–210 (1992)]. A recent study found that the renal clearance of PEG decreased with an increase in molecular weight, with the most dramatic change occurring at a MW of 30,000 after i.v. administration. The half-time (t1/2) of PEG circulating in blood also showed a concomitant and dramatic increase. For instance, the t1/2 for PEG went from approximately 18 min to 16.5 hour as the molecular weight increased from 6,000 to 50,000. Consequently, conjugation of anticancer drugs with PEG of a molecular weight of 20,000 or greater can prevent rapid elimination of the PEG-conjugated species and allow for passive tumor accumulation [Greenwald et al, Crit Rev Ther Drug Carrier Syst 17 (2), 101–61 (2000)].

In one embodiment of the present invention, a carboxyl group grafted PEG (20,000 Daltons or 25,000 Daltons containing 8 to 10 carboxyl groups per PEG molecule) is used as the starting material to conjugate with the cyclodextrins. In order to keep the steric hindrance effect to a minimum, CD moieties were conjugated at the small open end (6-position) of their cavity to the PEG backbone through one of the 7 primary hydroxyl groups. In addition, a flexible linear linker was used to keep the CD moiety away from the polymer backbone and allow it to move freely. Due to the biocompatibility of the materials and pliability of the polymers of the present invention, they will cause minimal toxicity and minimal mechanical irritation to the surrounding tissue.

A dosage form comprised of a solution of the grafted polymer that contains either dissolved drug or drug as a suspension or emulsion is administered to the body. The only limitation as to how much drug can be loaded into the formulation is one of functionality, namely, the drug load may be increased until the desired properties of the polymer are adversely affected to an unacceptable degree, or until the properties of the formulation are adversely affected to such a degree as to make administration of the formulation unacceptably difficult. Generally speaking, it is anticipated that in most instances the drug will make up between about 0.01% to 50% by weight of the formulation with ranges of between about 0.1% to 25% being most common. These ranges of drug loading are not limiting to the invention. Provided functionality is maintained, drug loadings outside of these ranges falls within the scope of the invention.

A distinct advantage to the compositions of the subject of this invention lies in the ability of the grafted polymer to increase the solubility and stability of many drug substances. The combination of hydrophobic CDs and hydrophilic polymers renders the polymer amphiphilic in nature. In that regard it functions much as a combination of cyclodextrin inclusion and polymeric micelle system. This is particularly advantageous in the solubilization of hydrophobic or poorly water soluble drugs such as cyclosporin A, tacrolimus, saquinavir and paclitaxel.

Another advantage to the composition of the invention lies in the ability of the polymer to increase the chemical stability of many drug substances. Various mechanisms for the degradation of drugs have been observed to be inhibited when the drug is in the presence of the polymer. For example, paclitaxel and cyclosporin A are substantially stabilized in the aqueous polymer composition of the present invention relative to certain aqueous solutions of these same drugs in the presence of organic co-solvents. This stabilization effect on paclitaxel and cyclosporin A is but illustrative of the effect that can be achieved with many other drug substances.

The drug loaded CD-grafted polymers of the present invention may be administered via various routes including parenteral, topical, transdermal, transmucosal, inhaled or inserted into a body cavity such as by ocular, vaginal, buccal, transurethral, rectal, nasal, oral, pulmonary and aural administration.

This invention is applicable to bioactive agents and drugs of all types including nucleic acids, hormones, anticancer-agents, and it offers an unusually effective way to deliver polypeptides and proteins. The only limitation to the polypeptide or protein drug which may be utilized is one of functionality. In some instances, the functionality or physical stability of polypeptides and proteins can also be increased by addition of various additives to aqueous solutions or suspensions of the polypeptide or protein drug. Additives, such as polyols (including sugars), amino acids, surfactants, polymers, other proteins and certain salts may be used. Developments in protein engineering may provide the possibility of increasing the inherent stability of peptides or proteins. While such resultant engineered or modified proteins may be regarded as new entities in regards to regulatory implications, that does not alter their suitability for use in the present invention.

In addition to peptide or protein based drugs, other drugs from all therapeutic and medically useful categories may be utilized. These drugs are described in such well-known literature references as the Merck Index, the Physicians Desk Reference, and The Pharmacological Basis of Therapeutics.

Paclitaxel is a diterpeniod natural product showing encouraging activity against ovarian, breast, head, and non-small-cell lung cancers. Recently it has been approved in the form of paclitaxel for treatment of breast and refractory human cancers. One of the major problems with paclitaxel is its extremely low aqueous solubility. The present formulation of this drug contains 30 mg of paclitaxel in 5 ml of a 50/50 mixture of Cremophore EL (polyethoxylated casteror oil, a solubilizing surfactant) and ethanol. When diluted in saline, as recommended for administration, the concentration of paclitaxel is 0.6–1.2 mg/ml (0.7–1.4 ml). The diluted solution is expected to contain mixed "micelle" particles of Paclitaxel/Cremophor and has been reported to be physically unstable over time, because dilution to some concentrations apparently yields supersaturated solutions. In addition, Cremophor, a non-charged surfactant, has been reported to cause histamine release and to be associated with adverse effects such as severe allergic reactions [Sharma et al, *Int J Cancer*, 71 (1), 103–7 (1997)]. Cyclodextrin derivatives have been examined to see if they can solubilize paclitaxel. It was found that methylated cyclodextrins worked much better than other hydrophilic cyclodextrin derivatives in improving the water solubility of paclitaxel (at 50% CD concentrations, HPCD and DMCD could dissolve about 0.7 and 33 mg/ml paclitaxel respectively) [Sharma et al. *J Pharm Sci*, 84 (10), 1223–30 (1995)]. However, the toxicity of DMCD and the high concentration needed to complex therapeutic levels of paclitaxel limit its clinical application. The CD-grafted amphiphilic polymers of the present invention provide significant advantages over prior art formulations facilitated by ease of preparation and administration, lowered toxicity, rapid and controlled release of active agents and targetable delivery.

Antisense oligonucleotides and their analogs, such as peptide DNA (PNA), morpholino-DNA, P-ethoxy DNA, methylphosphonate-DNA, etc., have been shown to have great applications in biomedical research, but their pharmaceutical applications have been largely limited by their stability and/or solubility, and cell uptake behavior. Currently there is no effective means to safely deliver intact antisense oligonucleotides to their target sites in vivo. And this is particularly true for their neutral analogs, such as PNA, morpholino DNA, P-ethoxy DNA and methylphosphonate-DNA, because they cannot efficiently bind to any of the current antisense oligonucleotide carriers which are mostly poly-cationic polymers. However, the CD-grafted amphiphilic polymers of the present invention can be effective carriers of neutral anologs because every nucleoside unit has an aromatic base residue which is a potential target to be included by the cyclodextrin, thus the CD-grafted polymers can bind oligonucleotides and their analogs through enhanced CD inclusion mechanisms. This binding can be very strong due to cooperation between the multiple CD moieties on the polymer and the multiple aromatic base rings on antisense oligonucelotides. In addition, extra ionic interactions (for charged oligonucleotide) or hydrophobic interactions (for non-charged oligonucleotide analogs) can also strengthen the binding between antisense oligonucelotides and CD-polymer carriers. Eventually the final binding complex may form a loose or tight polymeric micelle depending on their content, and therefore can safely deliver antisense oligonucleotides and their neutral analogs to cells.

In summary, the CD-grafted polymers of the present invention improve the drug/binding complex stability via multiple CD moiety co-operations and external hydrophobic or ionic interactions. It is likely that inclusion is an essential mechanism for the drug binding capability of the polymers of the present invention. However, ionic interactions and external hydrophobic interactions (outside the CD cavity) may also make significant contributions depending on the molecular structures of the specific co-polymers and guests. Furthermore, appropriately constructed PEG-CD co-polymers of the present invention are excellent paclitaxel solubilizers and carriers for safe therapeutic application. They can also be used as solubilizers and carriers for other hydrophobic drugs. The CD-grafted amphiphilic polymers of the present invention are water soluble and biocompatible, and have very slow release kinetics, especially when they contain high weight ratios of hydrophobic moieties. In addition, the strong binding constant of the drug/polymer complexes makes for slow release of the bound drug upon dilution, and it sometimes even needs replacement by other molecules. Therefore they may be used as ingredients in oral formulations for delivery of certain water soluble drugs.

Furthermore, properly constructed CD-grafted polymers of the present invention can be used to deliver antisense oligonucleotides and their non-charged analogs, as well as hydrophobic peptides and proteins, since external hydrophobic interactions may produce enough stability for hydrophobic antisense oligonucleotides or hydrophobic peptides. The negatively charged oligonucleotides are also expected to be good guest molecules for some specially constructed polymers, because a basic nitrogen in the linker of the polymer could neutralize negative charge under appropriate conditions.

The following Examples are presented to illustrate the process of preparing the composition and method of using the composition of the present invention.

EXAMPLE 1

Materials and methods: PEG with pendant propionic acid groups (PEG-10PA and PEG-8PA, Mw=~20 KD, SunBio, Inc., Anyang City, South Korea) was dried overnight in vacuo at room temperature. β-Cyclodextrin (TCI America, Portland, Oreg.) was dried in vacuo at 130° C. overnight before use. Other chemicals were from Aldrich Chemical Company, Inc. of Milwaukee, Wis.) and used as received without further purification. HPLC analysis was performed on a Waters system equipped with RI detector and Ultrahydrogel 120 and Ultrahydrogel 500 SEC columns. $^1$H-NMR was recorded on a Varian 400 MHz machine.

Synthesis of PEG-SS-CD (Compound 2)

Mono-6-(6-amino-3,4-dithio-hexylamino)-6-deoxy-β-cyclodextrin (Compound 1):

Cystamine dihydrochloride (1.0 g, 4.44 moles, Fw=225.2) was dissolved in 30 ml distilled water, followed by addition of 1.0 M KOH (8.88 moles) and mono-6-tosyl-β-cyclodextrin (0.5 g, Fw=1289) powder. The resulting suspension was stirred in a 70° C. oil bath overnight, then concentrated to about 4 ml. The mixture was applied on a Sephadex G-25 column (2.5×80 cm), eluted with 0.1 M TEA. About 0.38 g compound 1 was obtained.

PEG-SS-CD (Compound 2):

Carboxyl group grafted PEG (2.24 g, PEG-8PA, 20 kDa, polyethylene glycol containing 8 pendant propionic acid groups with average molecular weight of ~20,000) was dissolved in 25 ml anhydrous DMF, the mixture was cooled to 0° C. on ice under protection of argon. To this was added 280 ul of tributylamine (1.18 mmoles, Fw=185.36, d=0.778), followed by 175 ul of isobutylchloroformate (IBCF, Fw=136.6, d=1.053) in 1 ml DMF. The mixture was stirred at 0° C. for 1 hour. The reaction mixture was then slowly added to a solution of 1.75 g compound 2 in 100 ml DMF at room temperature. After being stirred at room temperature overnight, the reaction was stopped by addition of 1 ml water. The mixture was concentrated and then diluted with 60 ml water. The product solution was purified on a Sephadex G-50 column, eluted with 0.1 M TEA followed by ether precipitation. $^1$H-NMR analysis indicated that about 5 CD moieties were conjugated to a PEG backbone having a molecular weight of about 20,000 Daltons. The retention time of the product is about 0.45 minute later than that of the starting PEG as determined by HPLC chromatography [GPC column, Rt (product)=17.33', vs. Rt (PEG-8A)=16.87']. $^1$H-NMR (400 MHz, D2O): δ, 5.0 (s, 7H, H1'), 3.3–3.9 (m, 370H, 41H-CD, 329H-PEG).

EXAMPLE 2

Synthesis of PEG-SS-AcCD (Compound 3)

PEG-SS-CD (compound 2, 1.0 g, ~5 CDs/20 kD-PEG) was dried in a $P_2O_5$ desiccator, followed by co-evaporation with 50 ml anhydrous pyridine. The residue was dissolved in 30 ml pyridine under protection of argon, followed by addition of 2.0 ml acetic anhydride (Fw=102.1, d=1.08). The mixture was dried on a rotary-evaporator after being stirred at room temperature for 2 days. The crude product was purified by repeated ether precipitation from methanol. HPLC (GPC) analysis showed a 0.46 minute time delay of the product compared to the starting polymer (Rt=19.70' of the product vs. Rt=19.24' of the reactant polymer). $^1$H-NMR analysis indicates that each 20 kD PEG contains about 5 CD moieties and all hydroxyl groups are acetylated. $^1$H-NMR (400 MHz, $D_2O$): δ, 4.7–5.5(s, 14H, H1', H3'), 3.4–5.5 (m, 382H, 35H-CD, 347H-PEG), 2.05 (m, 20H, H-Ac).

EXAMPLE 3

Synthesis of PEG-SS-DECD (Compound 7)

PEG-SS-NH2 (Compound 4):

Carboxyl group grafted PEG (PEG-8PA, 2.6 g, 2.0 mmole COOH group) was dissolved in 30 ml anhydrous DMF and cooled to 0° C. on ice. To this was added tributylamine (0.35 ml, 1.5 mmoles, Fw=185.36, d=0.778), followed by the addition of isobutyl chloroformate (0.20 ml, 1.5 mmoles, Fw=136.6, d=1.053). The mixture was stirred at 0° C. for 80 minutes and was carefully added to a solution cystamine (3.5 g, Fw=152.2, 23 mmoles) in 50 ml anhydrous DMF. The mixture was stirred at room temperature for 20 hours, concentrated to about 20 ml on rotary evaporator at 40° C., then dialysed against distilled water (4×5 L over 26 hours, Sigma D-0655, MWCO=12,000) after being diluted with 50 ml water. The dialysis solution was concentrated by rotary evaporation at 40° C., obtaining 4.1 g of syrup. The syrup was dissolved in 10 ml methanol, then precipitated by addition of 80 ml ethyl ether. The precipitate was collected by centrifugation and this precipitation process was repeated twice. The final product was a white powder, weighing about 2.2 g. The product showed only one nice peak in its HPLC (GPC) chromatogram, and the retention time (18.66') was about 1.5 minutes longer than that of the starting PEG-8PA (17.11').

N-(β-Cyclodextrin-6-yl) Glycine Methyl Ester (Compound 5):

Glycine methyl ester hydrochloride (1.5 g, Fw=125.56, 12 mmoles, from Aldrich) was dissolved in 100 ml anhydrous DMF with protection of argon. To this was added DIPEA (2.1 ml, 12 mmoles, Fw=129.25, d=0.724), followed by the addition 6-mono-tosyl cyclodextrin powder (3.0 g, Fw=1289, ~80% pure, ~1.8 mmoles). The mixture was stirred at room temperature to a clear solution. The temperature was slowly raised to about 70° C. followed by another 4 hour stirring. The mixture was then concentrated to a syrup on a rotary evaporator at 55° C. The crude product was dissolved in 40 ml hot water, precipitated by adding ~80 ml acetone after cooled to room temperature. The white precipitate was collected by filtration and dried in a vacuum overnight. About 2.3 g of the desired compound 5 was obtained. This product was used in next step without further purification.

N-(Heptakis-2-O-ethyl-$6^B,6^C,6^D,6^E,6^F,6^G$-hexa-O-ethyl-β-Cyclodextrin-$6^A$-yl)-glycine (Compound 6):

N-(β-Cyclodextrin-6-yl) glycine methyl ester (compound 5 about 2.0 g, Fw=1206, ~1.6 mmoles) was dissolved in 15 ml DMSO and 15 ml DMF. The solution was cooled to 0° C. in an ice bath, followed by addition of 10 g BaO and 10 g Ba(OH)$_2$.H$_2$O with the protection of argon. To this white suspension was slowly added 20 ml diethyl sulfate. The mixture was stirred at 0° C. for 1 hour, followed by another 24 hour stirring at room temperature. Another 20 ml of diethyl sulfate was slowly added within an hour, followed by another 24 hour stirring at room temperature. To the viscous reaction mixture was slowly added 60 ml 5 N NaOH at 0° C., then the mixture was stirred at room temperature for one hour. It was extracted with 2×200 ml of chloroform. The combined organic phase was concentrated to a wax product after drying with Na$_2$SO$_4$. The crude product was dissolved in 20 ml methanol, followed by addition of 20 ml of distilled water. The mixture was filtered in vacuum to remove the trace amount of precipitate. The clear filtrate was concentrated to get an orange foam solid (about 1.8 g), which contained about 50% of the desired compound 6. This crude product was directly used in the next reaction after being dried overnight in vacuum P$_2$O$_5$ desiccator.

PEG-SS-DECD (Compound 7):

The crude compound 6 (1.4 g, ~0.46 mmole) was dried by co-evaporation with 2×20 ml anhydrous DMF, then re-dissolved in 20 ml DMF followed by addition of 0.19 ml tributylamine (0.8 mmole, Fw=185.36, d=0.778). The mixture was cooled to 0° C. on ice. To this cold solution was slowly added isobutyl chloroformate (60 ul, 0.46 mmole, Fw=136.6, d=1.053) in 2 ml DMF. The mixture was stirred at 0° C. for 1.5 hours, then transferred to a solution of PEG-SS-NH2 (compound 4, 4 g) in 10 ml anhydrous DMF at room temperature, followed by addition of DIPEA (28 ul, 0.16 mmole, Fw=129, d=0.724). The mixture was concentrated to a syrup after overnight stirring at room temperature. The syrup was triturated with 30 ml ethyl ether to produce an orange precipitate. The precipitate was collected by filtration and washed with ethyl ether. The solid was further purified twice by ether precipitation from methanol. About 0.55 g light orange solid was obtained. $^1$H-NMR indicated the product was the desired PEG-SS-DECD product, but only about 1.5 CD moieties were conjugated onto a 20-KD PEG molecule and about 13 ethyl groups per cyclodextrin. $^1$H-NMR (400 MHz, D2O): δ, 5.1 (7H, m, H1' and H3'), 3.2–3.9 (m, 1041H, 41H-CD, 1000H-PEG), 2.78 (m, 30H, CH2-Et), 1.15 (b, 45, CH3-Et).

EXAMPLE 4

Synthesis of PEG-GFLG-DECD (Compound 11)

Mono-6-(N$^3$-Boc-3-amino-propylamino)-6-deoxy-cyclodextrin (Compound 8):

Mono-Boc-1,3-diamino-propane (3.5 g, ~3.0 moles, Prepared according to the methods described by Jean Francois Pons et. al., Eur. J. Org Chem, 1998, 853–859) was dried by co-evaporation with 2.8 ml (12 mmoles, Fw=185.36, d=0.778) tributylamine and 30 ml anhydrous DMF twice. The final dried oil was mixed with 100 ml anhydrous DMF, followed by addition of DIPEA (2.1 ml, 12 mmole, Fw=129, d=0.742). To this solution was added 3.5 g of 6-mono-tosyl-6-O-β-cyclodextrin. The mixture was stirred at room temperature to the complete dissolution of the solid. Then the mixture was stirred overnight at 70° C. in an oil bath. The mixture was concentrated to about 10 ml on a rotary evaporator at 45° C., then precipitated with 100 ml of acetone. The white precipitate was collected by filtration, washed with acetone. About 3.2 g of product was obtained. It contained about 60% of the desired compound 8 as estimated on a TLC (Rf=0.12, Silica gel, developed in 80:10:10/AcOH:CHCl$_3$:H$_2$O, stained with 5% phosphomolybdic acid in 95% ethanol). This product was directly ethylated in the next step.

Mono-(Heptakis-2-O-ethyl-$6^B,6^C,6^D,6^E,6^F,6^G$-hexa-O-ethyl-β-Cyclodextrin-$6^A$-yl)-1,3-diamino-propane (Compound 9):

Mono-6-(N$^3$-Boc-3-amino-propylamino)-6-deoxy-β-Cyclodextrin (Compound 8, 3.0 g) was dissolved in 40 ml anhydrous DMF and 40 ml DMSO at 0° C., then mixed with 10 g of BaO and 10 ml of Ba(OH)$_2$.H$_2$O under protection of argon. The mixture was cooled to 0° C., then 20 ml of diethyl sulfate was slowly added. The mixture was stirred at 0° C. for 6 hours followed by another 2 days at room temperature. To the reaction mixture was added 25 ml of cold ammonia followed by another 3 hour stirring at room temperature. The final reaction mixture was diluted with 50 ml H$_2$O, extracted with 3×100 ml ethyl acetate. The organic phase was thoroughly washed with 2×200 ml saturated NaHCO$_3$ and 3×200 water, then concentrated after drying with sodium sulfate. About 2.8 g of orange solid was obtained after being dried in vacuum overnight. The product was dissolved in 10 ml of trifluoroacetic acid. The clear solution was stirred at room temperature for 3 hours, then 15 ml of water was added. The mixture was stirred at room temperature for another 20 minutes, then dried on a rotary evaporator at 45° C. The residue was dissolved in 150 ml ethyl acetate, washed with 3×100 ml saturated $NaHCO_3$ and 100 ml of saline. The organic phase was concentrated after being dried with $Na_2SO_4$. About 2.0 grams of crude compound 9 was obtained. This product was directly used in the next conjugation reaction.

PEG-GFLF (SEQ ID NO:1)-DECD (Compound 11):

PEG-GFLG (SEQ ID NO:1)(tetrapeptide Gly-Phe-Leu-Gly (SEQ ID NO:1) grafted PEG polymer, compound 10, ~4.5 GFLG (SEQ ID NO:1) peptide in a PEG of 20,000 prepared from PEG-8PA and GFLG (SEQ ID NO:1) peptide) (2.0 g, ~0.4 mmole —COOH, dried by co-evaporation with 30 ml DMF) was dissolved in 30 ml anhydrous DMF and 0.17 ml of tributylamine (0.7 mmole, Fw=185.36, d=1.053) with protection of argon. To this was added 0.078 ml (0.6 mmole) isobutylchloroformate in 2 ml DMF after cooling to 0° C. The mixture was stirred at 0° C. for 1.5 hours, then slowly added to the solution of 2.0 g compound 9 in 20 ml DMF at room temperature, followed by addition of 0.087 ml of DIPEA (0.5 mmole). The mixture was stirred at room temperature overnight, concentrated to about 10 ml, precipitated with 90 ml of cold ethyl ether. The orange precipitate was collected by filtration and was further precipitated 3 times using ether from methanol. The final product was about 2.2 grams. The retention time of the product (Rt=18.42') was 0.67 minutes longer than that of the starting PEG-GFLG (SEQ ID NO:1) polymer (Rt=17.76') on HPLC (GPC) chromatography. $^1$H-NMR indicates the product is the desired compound 11: every 20 kD polymer contains about 4.5 tetrapeptide GFLG (SEQ ID NO:1) and 1.8 CD moieties and every CD moiety has about 13 ethyl groups. $^1$H-NMR (400 HMz, $D_2O$): δ, 7.20 (5H, m, ArH-Phe), 5.1 (2.8H, m, H1'-CD), 3.0–4.0 (645H, m, 41H-CD, 574H-PEG, 30H-Et), 1.1 (15.6H,m, 30H, CH3-Et), 0.9 (6H, d, CH3-Leu).

EXAMPLE 5

Synthesis of PEG-C3-AcCD, PEG-C3-DECD and PEG-C3-BnCD

Mono-6-(γ-amino-propanyl-amino)-6-deoxy-β-cyclodextrin (Compound 12):

Mono-6-tosyl-6-deoxy-cyclodextrin (6.5 g, Fw=1269) was dissolved in 200 ml of anhydrous DMF and 60 ml of diaminopropane under vigorous stirring at room temperature. The clear mixture was stirred at room temperature for 2 hours followed by another 20 hours at 65° C. C. The mixture was concentrated to about 20 ml at 45° C. C. To this was added 200 ml of cold isopropanol at room temperature. The white precipitate was collected by filtration. The solid was re-dissolved in 25 ml water and 25 ml TEA. To this was slowly added 300 ml of acetone at 0° C. C. The precipitate was collected by filtration, and re-precipitation was repeated two-more times. The final product was about 5.5 grams. It contains about 80% of the desired compound 12 and about 20% free cyclodextrin. The product was used for the next reaction without further purification.

PEG-C3–D (compound 13): Mono-6-(γ-amino-propanyl-amino)-6-deoxy-β-cyclodextrin (compound 12, 6.2 g) was conjugated to PEG-8PA (4.1 g) using the same method as described in the synthesis of PEG-SS-CD. About 4.3 g of pure product was obtained after GPC purification. The retention time of the product (17.87') is 0.76 minute longer than that of starting PEG-8PA (17.11'). $^1$H-NMR indicates the product is the desired compound 13, which contains about 4.5 CD moieties in every 20 KD PEG molecule. $^1$H-NMR (400 HMz, D2O): δ, 5.0 (7H, s, H1'-CD), 3.4–3.9 (412H, m, 41H-CD, 371H-PEG).

PEG-C3-AcCD (compound 15): PEG-C3–D (1.0 gram, ~4.5 CDs/20 KD PEG) was acetylated using the same method as described in the preparation of PEG-SS-AcCD. About 1.0 gram of product was obtained and its retention time (17.99') was only about 7.2 seconds longer than that of the starting polymer (PEG-C3–D, 17.87'). However $^1$H-NMR indicated that the product is the desired compound 15: the polymer contains 4.5 of CD moieties in every 20 kD PEG and bout 90% of the hydroxyl groups on the pendent CDs were acetylated. $^1$H-NMR (D2O): δ, 4.9–5.4 (14H, m, H1'-CD and H3'-CD), 3.2–4.5 (m, 490H, 35H-CD, 455H-PEG), 2.03 (d, 64H, $CH_3CO$—).

PEG-C3-BnCD (compound 16): PEG-C3–D (Compound 13, 0.9 g, ~4.5 CDs/20 KD PEG) was dried by co-evaporation with 20 ml anhydrous pyridine and then re-dissolved in 30 ml pyridine with protection of argon. To this was slowly added 3 ml of butyryl chloride (Fw=106.55, d=1.026) at room temperature (cooled with ice as the reaction temperature went up). Methanol (5.0 ml) was added after the mixture was stirred at room temperature for 4 hours, followed by another 30 minutes of stirring at room temperature. The mixture was concentrated on a rotary evaporator to a wax solid. The solid was dissolved in 20 ml of methanol, and diluted with 20 ml water. The clear solution was dialyzed against 2×5 L 20% isopropanol/water. The opaque dialysis solution was concentrated in a Speed-Vac at room temperature. The pellet was further precipitated three times from methanol using ether. The product is practically insoluble in water, but very soluble in methanol or chloroform. Yield=90%. $^1$H-NMR indicates that the product is the desired compound 16: about 80% of the hydroxyl groups on the pendant cyclodextrins were butyrylated. $^1$H-NMR ($CDCl_3$): δ, 4.6–5.3 (14H, m, H1' and H3'), 3.2–4.5 (m, 541, 35H-CD, 486H-PEG), 2.30 (m, 36H, $CH_3CH_2CH_2CO$—, 1.65 (m, 36H, $CH_3CH_2CH_2CO$—), 0.95 (m, 54H, $CH_3CH_2CH_2CO$—).

EXAMPLE 6

Synthesis of PEG-L8-AcCD and PEG-L8-DECD

Mono-6-(8-amino-3,6-dioxy-octylamino)-6-deoxy-β-cyclodextrin (Compound 17):

In a 500 ml round bottom flask was charged with 2,2'-(ethylenedioxy)bis(ethylamine) (300 ml, Fw=148) and mono-6-tosyl-β-cyclodextrin (24.4 g, Fw=1269, dried in a $P_2O_5$ desiccator overnight) under the protection of argon. The suspension was stirred at room temperature to the complete dissolution of all of the solid (~1.0 hour). The mixture was stirred for another 4 hours at 75° C. The reaction mixture was slowly poured into 1.8 L of cold isopropanol. The precipitate was collected by filtration and washed with isopropanol. The precipitate was dissolved in 200 ml warm water (50° C.), then slowly poured into 1.8 L of ice cold isopropanol with stirring. The precipitate was collected by filtration after being cooled to −20° C. This isopropanol precipitation process was repeated two more times. About 24 grams of white powder was obtained. HPLC analysis (GPC, eluted with 0.1 M $NaNO_3$) showed that the product contains about 85% desired compound (Rt=39.21') and ~15% non-modified 1–D (Rt=32.25'), no free diamine reactant was detected. So this product was directly used for next conjugation. $^1$H-NMR (400 HMz, D2O): δ, 4.97 (7H, m, H1'), 3.7–3.9 (26H, m, 7H3', 7H5', 6H6', 6H6''), 3.3–3.6 (24H, m, 7H2/, 7H4', 1H6', 1H6'', 8H-linker), 2.71 (4H, m, $CH_2N$-linker).

PEG-L8–D (Compound 18):

PEG-8PA (4.0 g, ~8–OOH/PEG-20K, ~1.7 mmoles COOH, dried in a $P_2O_5$ desiccator overnight and co-evaporated with 50 ml anhydrous DMF) was dissolved in 50 ml anhydrous DMF and 0.54 ml tributyl amine (TBA, Fw=185.36, d=0.778, 2.27 mmoles). The clear mixture was cooled on ice, then 0.29 ml isobutyl chloroformate (IBCF, Fw=136.6, d=1.053, 2.2 mmoles) was added at 0° C. The mixture was stirred at 0° C. for 1 hour, and was then slowly added to a solution of mono-6-(8-amino-3,6-dioxy-octylamino)-6-deoxy-β-cyclodextrin (compound 17, 5.0 g, Fw=1336, ~80% pure, ~2.6 mmoles, dried in a $P_2O_5$ desiccator overnight) in 50 ml anhydrous DMF at room temperature. After overnight stirring, the mixture was concentrated to about 20 ml on a rota-vap at 50° C. The mixture was diluted with 60 ml of water and purified on a Sephadex-G-50 column (2.5×80 cm, eluted with 0.1 M TEAA, pH=10.0, collected 8 ml/ml). The fractions were analyzed by GPC-HPLC and the polymer fraction was pooled into two parts: Part A: fraction 9 through 30; Part B: fraction 31 through 35.

Both parts were concentrated to wax solids on rotary evaporator and then re-dissolved in 15 ml methanol. The products were precipitated by 5 ml TEA and 120 ml of ethyl ether. The white precipitates were collected by filtration. Part A and Part B weighed 4.7 gram and 0.55 gram, respectively. $^1$H-NMR analysis confirmed both parts were the desired PEG-L8–D product, but with different cyclodextrin loading: on average a 20 KD-PEG polymer contains about 5.5 and 8.5 cyclodextrin moieties in part A and part B, respectively. $^1$H-NMR (400 MHz, D2O): δ, Part A: 5.0 (s, 7H, H1'), 3.3–3.9 (382H, m, 41H-CD, 12H-linker, 329H-PEG; Part B: 5.0 (s, 7H, H1'), 3.3–3.9 (256H, m, 41H-CD, 12H-linker, 203H-PEG).

PEG-L8-AcCD (Compound 19):

PEG-L8–D (Compound 18, 1.0 g, 5.5 CDs/20 KD PEG, dried in P2O5 desiccator overnight) was dried by co-evaporation with 40 ml anhydrous pyridine, then re-dissolved in 40 ml anhydrous pyridine under protection of argon. To this was added 3.0 ml acetic anhydride. The mixture was stirred at room temperature for 2 days, concentrated to about 10 ml on a rotary evaporator at 45° C. To this was slowly added 90 ml of ethyl ether. The precipitate was collected by filtration. The product was further purified by ether precipitation three more times from methanol. The final white powder was dried in a vacuum, and it weighed 1.07 g. $^1$H-NMR confirmed the product is the desired product 19: Every 20 kD PEG contains about 5.5 CD moieties and about 90% of the hydroxyl groups on the pendent CD moieties of the polymer were acetylated. $^1$H-NMR (D2O): δ, 4.9–5.4 (14H, m, H1'-CD and H3'-CD), 3.2–4.5 (m, 422H, 34H-CD, 12H-linker, 376H-PEG), 2.03 (d, 64H, CH3CO—).

PEG-L8-DECD (Compound 20):

PEG-L8–D (compound 18, 1.0 g, ~5.5 CDs/20 KD PEG, dried in $P_2O_5$ desiccator overnight) was dissolved in 5 ml anhydrous DMSO and 5 ml anhydrous DMF, the solution was cooled to 0° C. on ice under protection of argon. To this was added 0.75 g BaO and 0.75 g $Ba(OH)_2.H_2O$ powder, immediately followed by addition of 3 ml of diethyl sulfate in three portions over a one hour period. The suspension was stirred at 0° C. for 2 hours, followed by stirring for another 2 days at 4° C. Then 80 ml of cold ethyl ether was added at 0° C., followed by another 30 minutes of stirring at 0° C. The orange precipitate was collected by filtration and dissolved in 50 ml 50% methanol/water. The mixture was dialyzed (MWCO=12,000) against 5 L of 0.01 N HCl, then 2×5L water. The final dialysis solution was concentrated, obtaining about 1 g of wax product. It was further purified by ether precipitation from methanol twice. $^1$HNMR analysis indicated that about 4 CDs are present in every 20 KD-PEG, and each CD moiety carries about 11 ethyl groups. This means about 30% of the CD moieties came off the PEG backbone during the alkylation process. $^1$H-NMR (400 HMz, D20): δ, 4.9–5.3 (7H, m, H1'-CD), 3.1–4.0 (540H, m, 41H-CD, 469H-PEG, 8H-linker, 22H-CH2-ehthyl), 1.2 (33H, m, CH3-ethyl)

Figure 4:
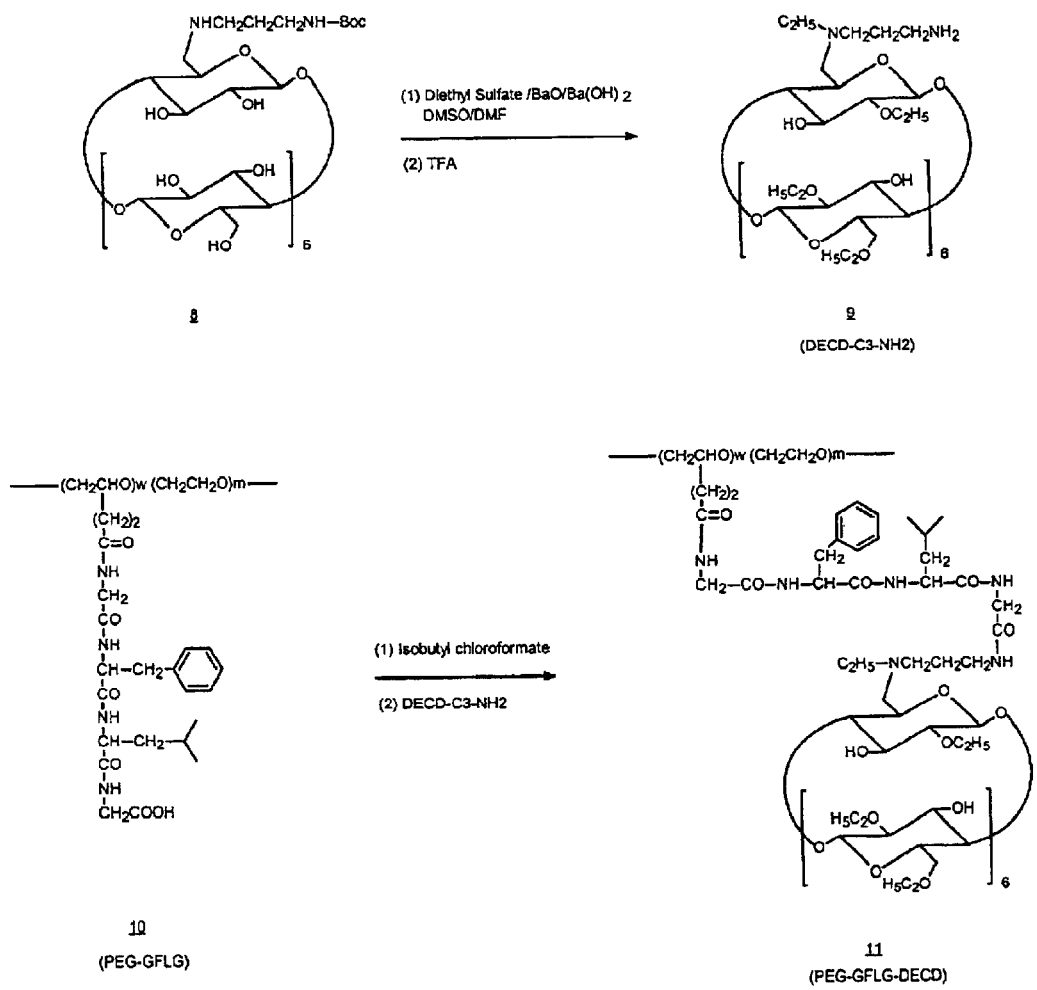
FIG. 4 depicts a reaction scheme for synthesis of PEG-GFLG (SEQ ID NO:1)-DECD.
Figure 5:
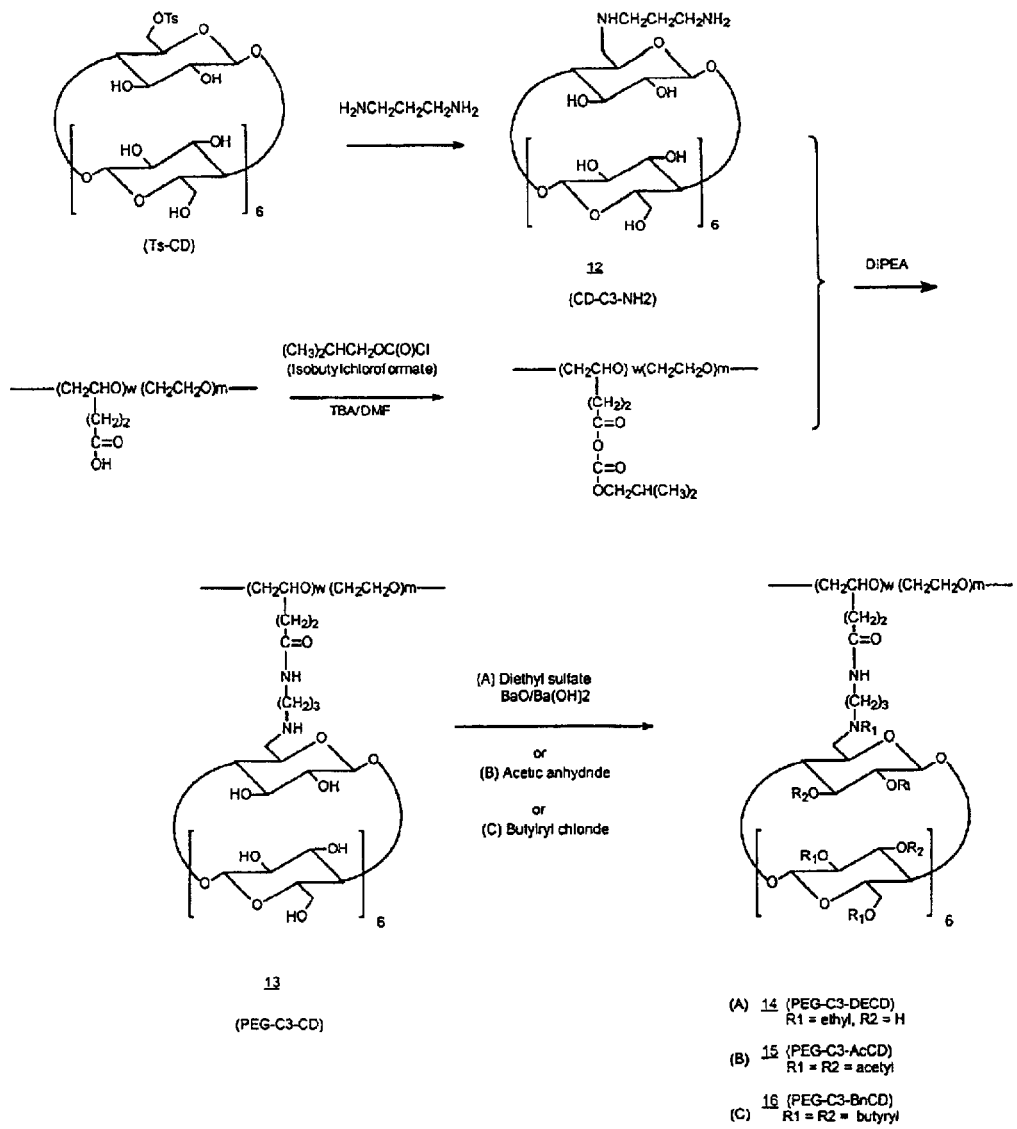
FIG. 5 depicts a reaction scheme for synthesis of PEG-C3-AcCD, PEG-C3-DECD and PEG-C3-BnCD.
Figure 6:
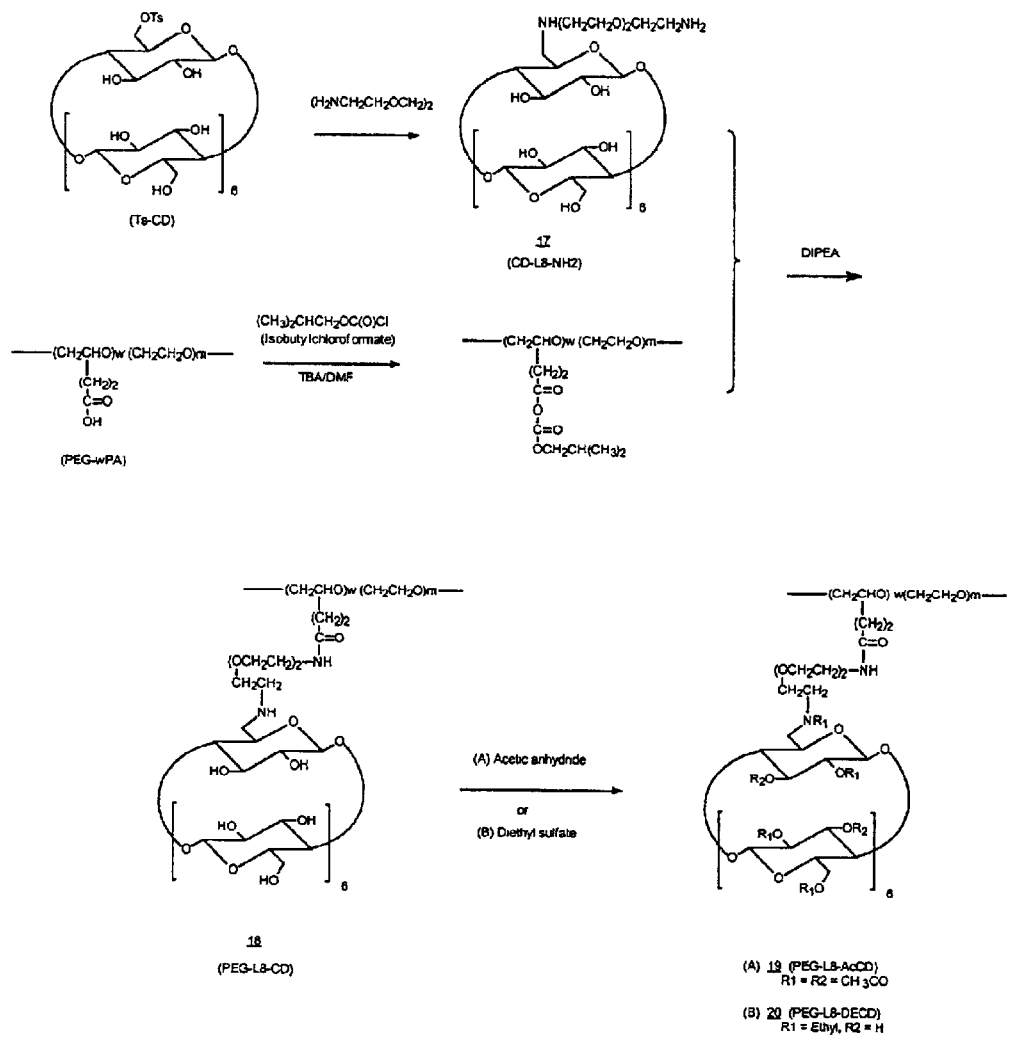
FIG. 6 depicts a reaction scheme for synthesis of PEG-L8-AcCD, PEG-L8-DECD.

Thirteen representative cyclodextrin-grafted-PEG polymers (Table 1) have been prepared according to Examples 1–6 and FIG. 4-8, wherein the linkers are either biodegradable (X=SS— or -GFLG (SEQ ID NO:1) or non-biodegradable (—C3- or -L8-). The pendent cyclodextrin moieties are either natural β-CD (PEG-X-CD) or modified with hydrophobic groups including ethyl (PEG-X-DECD), acetyl (PEG-X-AcCD) or butyryl (PEG-C3-BnCD). GPC-HPLC was used to monitor each step of the preparation process, and it was found that all final polymer products had longer retention times than the corresponding PEG precursors. The structure of all of the product polymers were confirmed by $^1$H-NMR analysis, it was found that their CD contents varied from an average of 1.5 CDs to 8.5 CDs on every 20 KD PEG backbone (Table 2). They are all highly soluble in most organic solvents (chloroform, methanol, ethanol, etc.). They are also highly soluble in water, except PEG-C3-BnCD.

TABLE 2

Structure characteristics of some cyclodextrin grafted PEG co-polymers

| Polymer name | $t_R$ (min*) | Number of CDs/ 20 Kd Polymer** | CD modification** |
|---|---|---|---|
| PEG-ss-CD | 19.34 | 3.9 | None |
| PEG-ss-AcCD | 19.24 | 3.9 | ~100% acetylation |
| PEG-C3-CD | 18.07 | 4.8 | None |
| PEG-C3-AcCD | 17.86 | 4.8 | ~80% acetylation |
| PEG-L8-CD (A) | 18.12 | 4.6 | None |
| PEG-L8-AcCD (A) | 17.98 | 4.6 | ~95% acetylation |
| PEG-L8-CD (B) | 18.43 | 5.9 | None |
| PEG-L8-AcCD (B) | 18.08 | 5.9 | ~84% acetylation |
| PEG-L8-CD (C) | 18.71 | 5.4 | None |
| PEG-L8-AcCD (C) | 18.53 | 5.4 | ~100% acetylation |
| PEG-GFLG-DECD | | 2.5 | ~67% ethylation |
| PEG-L8-DECD | 18.0 | 3.9 | ~67% ethylation |
| PEG-C3-BnCD | | 4.5 | ~80% Butyrylation |

In Table 2 above GFLG is (SEQ ID NO:1).
*GPC columns of Waters Ultrahydrogel (120 & 500), eluted with 0.1 M NaNO3;
**Calculated according to $^1$H-NMR spectrum recorded on a Varian 400 HMz;

In Table 2 above GFLG is (SEQ ID NO:1).

EXAMPLE 7

Preparation of Paclitaxel Complexes with CD Polymers or CD Monomers (A) Co-dissolving Method: This Method is Suitable for all Complexes with Water Soluble Polymers The aqueous solution of polymer (or monomer controls) (usually about 100 mg/ml) was mixed with equal volume (usually 40 to 2000 ul) of the paclitaxel solution ($C_{paclitael}$= 0.1 to 8.0 mg/ml in methanol). The mixture was incubated at room temperature for about half an hour. Then the solvents were removed in a centrifuge concentrator at room temperature. The concentrated syrup or wax solid was reconstituted by adding water or PBS buffer to the original volume. The mixture was usually a clear or slightly cloudy solution after 30 minutes of reconstitution. The un-dissolved paclitaxel particles were removed either by ultra-filtration (0.2 um filter) or by centrifugation (20 minutes at 20,800 g and room temperature). The paclitaxel concentration in the clear supernatant was quantified by UV absorbance at 290 nm by using the corresponding cyclodextrin polymer solution as the background calibration.

(B) Dialysis Method: This Method is Suitable for the Preparation of all Paclitaxel/polymer Complex Solutions:

The methanol solution of the polymer (usually 1100 mg/ml) was mixed with equal volume (100 ul) of paclitaxel solution (1 to 3 mg/ml in methanol). The clear mixture was incubated at room temperature for about half an hour at room temperature, followed by dialysis (MWCO=12,000) overnight against 2 L water. The dialysis solution was usually a clear solution. Trace amounts of paclitaxel particles were removed either by ultra-filtration (0.2 um filter) or by centrifugation (20 minutes at 20,800 g and room temperature). The clear solution was stored at 4° C. or below.

EXAMPLE 8

Preparation of Antisense Oligonucleotide/CD-polymer Complexes

Cyclodextrin PEG polymers (50 mg/ml) were mixed with a certain amount of a 21-mer-fluorescent labeled oligonucleotide in 20 mM Tris-HCl buffer (pH=7.4). The solutions were dried in a Speed-Vac, followed by reconstitution using the same amount of water. The DNA/polymer complexes in the solution were analyzed using 1% agarose gel in pH=7.4 TAE buffer.

TABLE 3

Comparison of Paclitaxel or Oligonucleotide Loading by some of the co-polymers as compared with other available CD derivatives

| Polymer | CD moiety/ loading Polymer | Paclitaxel loading (mg/50 mg polymer*) | Oligonucleotide (mg/50 mg polymer*) |
|---|---|---|---|
| PEG-ss-CD | 3.9 | <0.05 | ND** |
| PEG-ss-AcCD | 3.9 | 0.8 | ND |
| PEG-C3-CD | 4.8 | <0.05 | ND |
| PEG-C3-AcCD | 4.8 | ~2.0 | ND |
| PEG-L8-CD (A) | 4.6 | <0.05 | ND |
| PEG-L8-AcCD (A) | 4.6 | ~2.6 | ND |
| PEG-L8-CD (B) | 5.9 | <0.05 | ND |
| PEG-L8-AcCD (B) | 5.9 | ~2.9 | ND |
| PEG-ss-DECD | 1.5 | 0.4 | ~0.06 |
| PEG-GFLG-DECD | 2.5 | 3.0 | ~0.2 |
| PEG-C3-DECD | 2.6 | <1.0 | ~0.15 |
| PEG-L8-DECD | 3.9 | <1.0 | ~0.2 |
| Controls | | | |
| HP-CD (from Sigma) | | <0.05 | |
| (SBE)$_7$-CD (from Cydex) | | <0.05 | |
| DM-CD (from Sigma) | | ~0.2 (at day 1) | |
| EP-CD (from Sigma) | | <0.05 | |

In Table 2 above GFLG is (SEQ ID NO:1).
*Drug amount in 1.0 ml water or PBS in the presence of 50 mg of polymer or other CD derivatives.
**None detectable.

In Table 3 above GFLG is (SEQ ID NO:1)

EXAMPLE 9

Stability of Taxol/CD Complexes in 50% Serum or After 10 Fold Dilution in PBS:

(A) Stability in 50% fetal bovine serum: Taxol/PEG-L8-AcCD (2.0 mg/50 mg in 1.0 ml PBS buffer) or Taxol/DMCD (0.5 mg/50 mg in PBS buffer) complex solutions were prepared as describe in method A of example 7. Fifty micro liters of the complex solutions were diluted with equal volume of fetal bovine serum respectively. Both mixtures were centrifuged at 20,8000 g at room temperature after incubation at room temperature for 2 hours, 21 hours, 49 hours and 144 hours, respectively. The Taxol concentration in each supernatant was quantified by measuring the UV absorption at 230 nm.

(B) Stability after 10 fold dilution with PBS: Taxol/PEG-L8-AcCD (2.0 mg/50 mg in 1.0 ml PBS buffer) or Taxol/DMCD (0.5 mg/50 mg in PBS buffer) complex solutions were prepared as describe in example 10. Fifty micro liters of the complex solutions were diluted with 450 micro liter of PBS buffer, respectively. Both mixtures were centrifuged at 20,8000 g at room temperature after incubated room temperature for 2 hours, 21 hours, 49 hours and 144 hours. The Taxol concentration in each supernatant was quantified by measuring the UV absorption at 230 nm.

TABLE 4

Summary of the Stability Test of Pacitaxel/PEG-L8-AcCD and Pacitaxel/DMCD complexes in 50% Serum or after dilution with PBS

| | Remaining paclitaxel % in diluted solution | | | |
|---|---|---|---|---|
| Time (hour) | PEG-L8-AcCD 50% Serum | PEG-L8-AcCD 10X PBS | DMCD 50% Serum | DMCD 10X PBS |
| 0 | 100 | 100 | 100 | 100 |
| 2 | 100 | 100 | 100 | 86 |
| 21 | 97 | 100 | 100 | 13 |
| 49 | 92 | 99 | 100 | |
| 144 | 84 | 79 | 100 | |

EXAMPLE 10

Release of Paclitaxel from the Paclitaxel/PEG-L8-AcCD Complexes and the Cytotoxicity of the Free Co-polymers The efficient release of the free paclitaxel from its PEG-L8-AcCD complex was confirmed by the cytotoxicity of the complexes. Similar $IC_{50}$ values were obtained for both paclitaxel/PEG-L8-AcCD complex formulation (in this invention) and current commercial Paclitaxel/Cremophor formulation (Taxol, Bristol-Myers Squibb) in all three tested cell lines as determined by modified MTT assay as described below. But PEG-L8-AcCD alone showed no detectable cytotoxicity at the highest testing concentration while cremophor killed half of the cells at a concentration of about 0.5 mg/ml (Table 5):

1. Cells were plated at about 5,000 cells/well in 96-well plates in 0.1 ml medium and incubated at 37° C. for 24 hours;
2. Remove the old medium, add 80 ul of fresh media to each well;
3. Add 20 ul of sample solutions to each well (5×serially diluted, at least 8 concentrations for each sample)
4. The cells were incubated 3 or 4 days;
5. The media was removed. Added 80 ul of fresh media with 20 ul of MTS solution (Promega CellTiter 96 Aqueous One Solution Reagent #G358A). Incubate 37° C. for 2 to 4 hours;

6. Read absorbance at 490 nm on plate reader

7. Calculate the $IC_{50}$ using cell free well as blank control and drug free well as 100% viability control.

TABLE 5

Comparison of the $IC_{50}$* of different Taxol formulations and carrier controls in three different cell lines

| Formulations | $IC_{50}$ (ng/ml) | | |
|---|---|---|---|
| | Hela | HT1080 | MCF7 |
| Paclitaxel/ PEG-L8-AcCD | 3.0 | 2.0 | 2.0 |
| Paclitaxel/ Cremophor | 3.0 | 4.0 | 2.0 |
| Cremophor | 500,000 | 500,000 | 500,000 |
| PEG-L8-AcCD | >10,000,000 | >10,000,000 | >10,000,000 |

*Concentration at which cells have 50% viability as evaluated by modified MTT assays:

EXAMPLE 11

Hemolysis Activity of the Co-polymers and Their Possible Biodegradation Products:

To further investigate the cytotoxicity of our polymers and their possible biodegradation products, their hemolysis effects were tested on fresh human blood cells in comparison with commercial CD monomers as describe below. The degree of hemolysis was reported as a percentage of the total efflux of hemoglobin in distilled water (Table 6)

1. Red blood cells were isolated from whole human blood by centrifugation at 1000 g for 10 minutes.

2. The plasma was removed and the red blood cells re-suspended in normal buffed saline (PBS, 0.154 M sodium chloride and 0.01 M phosphate, pH=7.4). The red blood cells were pelleted by centrifugation (1000 g for 10 minutes).

3. Step 2 was repeated twice to remove the heme released from damaged cells.

4. The final pellet was diluted with PBS to give a hematocrit of approximately 12 (or 5%) as determined by centrifugal sedimentation.

5.2 ml of polymer or cyclodextrin solutions of a series of concentrations from 0 to 50 mg/ml in PBS buffer) equilibrated at 37° C. in PBS buffer were equilibrated at 37° C. To this was added 100 ul of a red blood cell suspension followed by mixing of the sample with gentle inversion. The samples were incubated for 30 minutes at 37° C.

6. The intact cells and cellular debris were pelleted by centrifugation at 1000 g for 5 min. The supernatant was analyzed spectrophotometrically at 543 nm for released heme.

TABLE 6

Comparison of Hemolysis activities of different PEG-CD polymers and their precursor monomers with commercial CD derivatives.

| Comopmers or CD monomers | Hemolysis ($HC_{50}$, mM) |
|---|---|
| PEG-L8-AcCD | ND |
| PEG-L8-DECD | ND |
| PEG-L8-CD | ND |
| CD-L8-NH2 | 25 |
| (SBE)$_7$-CD | ND |
| DM-CD | 1.0 |
| βCD | 4.0 |
| HPβCD | 35 |

The above data show that the novel PEG-CD polymers of the present invention have great potential to be used as safe drug carriers for paclitaxel (Table 3, Table 4, Table 5 and Table 6). In the presence of 50 mg/ml of the polymers, the paclitaxel can be dissolved in water at a concentration of at least 2.2 mg/ml, which is more than a 10,000 fold increase in free paclitaxel water solubility, and at least 1,000 and 20 times better than that of hydroxylpropyl-β-cyclodextrin (HPCD) and methyl-β-cyclodextrin (DMCD), respectively, under similar conditions [Sharma et al. *J Pharm Sci*, 84 (10), 1223–30 (1995)]. This dramatic solubility increase may due to a combination of at least the following three factors: 1) increased local concentration of CD moieties; 2) increased binding constant by cooperation the structure of paclitaxel has three phenyl groups around a large, fused taxane ring system); and 3) extra hydrophobic interactions outside the CD cavities.

As expected, after being conjugated to PEG polymer, the toxicity of β-cyclodextrin was significantly reduced. No cytotoxicity was detected on all the cyclodextrin pendent PEG polymers as identified on MTT and hemolysis assays (Table 5 and Table 6). Even the monomer (building block) was much less toxic than natural β-cyclodextrin. On another hand, because the weight ratios of CD moieties in our current co-polymer were only less than 25% as determined by $^1$H-NMR, the actual CD concentration in our experimental concentration (50 mg co-polymer/ml water) was less than 12.5 mg/ml. In another words, the weight ratio of cyclodextrin: Paclitaxel moiety was less than 6:1 in the current polymer complexes. Therefore, the co-polymers with non-biodegradable linkers are very safe drug carriers with very efficient drug release characteristics (Table 5). Additionally, the biodegradable linkage may also be acceptable as necessary to accelerate drug release.

The above Examples are presented for illustrative purposes only and are not intended, and should not be constructed to limit the invention in any manner. Various modifications of the compounds and methods of the invention may be made without departing from the spirit or scope thereof and it is to be understood that the invention is intended to be limited only as defined in the appended claims.

We claim:

1. A cyclodextrin grafted biocompatible polymer having the formula 1:

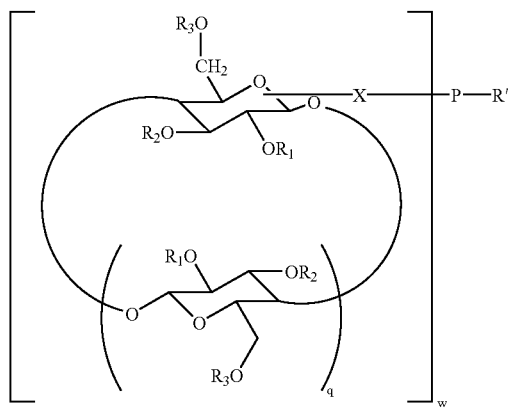

wherein P is a biocompatible hydrophilic polymer backbone having a molecular weight range from 2,000 to 1,000,000 Daltons; R' is H or a targeting moiety; X is a linker having the formula

-Q-Z-Q'- wherein Q is covalently bonded to the hydrophilic polymer backbone either directly or by means of a pendant alkyl or other functional group and Q' is covalently bonded to the cylodextrin at the 2, 3 or 6 position thereby replacing either an $OR_1$, an $OR_2$ or an $OR_3$ group respectively; Q and Q' are independently members selected from the group consisting of $NR_4$, S, O, CO, CONH, and COO; Z is a member selected from the group consisting of an alkylene disulfide, $[-(CH_2)_a\ S-S(CH_2)_a-]$, an alkylene $[-(CH_2)_a-]$, an alkylene oxide $(-[(CH_2)_aO]_b(CH_2)_a-)$, or a peptide linker, where a is an integer of 1 to 10 and b is an integer of 1 to 20; $R_1$, $R_2$, $R_3$ and $R_4$ are independently members selected from the group consisting of H, alkyl $(C_nH_{2n'+1})$, alkenyl $(C_{n'+1}H_{2(n'+1)-1})$ or acyl $(C_{n'}H_{2n'+1}CO)$ where n' is an integer of 1 to 16; q is an integer of 5, 6 or 7; and w is an integer such that each biocompatible hydrophilic polymer backbone contains between 1.5 and 30 cyclodextrin moieties per 20 KD of biocompatible hydrophilic polymer backbone.

2. The cyclodextrin grafted biocompatible polymer of claim 1 wherein the biocompatible hydrophilic polymer backbone is a member selected from the group consisting of polyethylene glycol (PEG), N-(2-hydroxypropyl) methacrylamide polymer (HPMA), polyethylenimine (PEI), polylysine, and derivatives thereof.

3. The cyclodextrin grafted biocompatible polymer of claim 2 wherein each biocompatible hydrphilic polymer backbone contains between 2 and 15 cyclodextrin moieties per 20 KD of polymer backbone.

4. The cyclodextrin grafted biocompatible polymer of claim 3 wherein the biocompatible hydrophilic polymer backbone has a molecular weight of between about 5,000 and 70,000.

5. The cyclodextrin grafted biocompatible polymer of claim 4 where Q is C(O)NH, Q' is $NR_4$ and a is 2.

6. The cyclodextrin grafted biocompatible polymer of claim 4 where Z is $-(CH_2)_2S-S(CH_2)_2-$; $R_4$ is $C_2H_5$; $R_1$ is $C_2H_5$; $R_2$ is H and $R_3$ is $C_2H_5$.

7. A cyclodextrin grafted biocompatible polymer having the formula 2

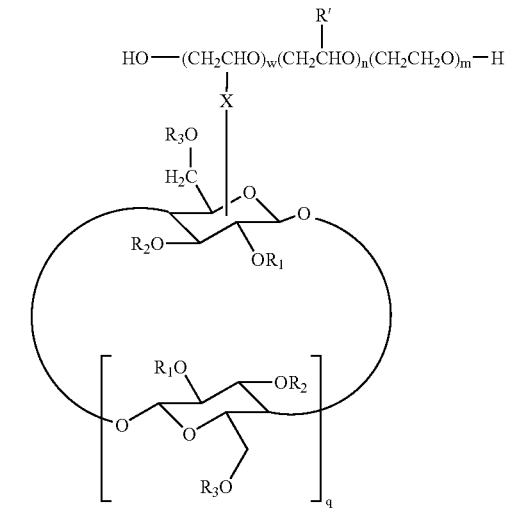

wherein R' is H or a targeting moiety; X is a linker having the formula

-Q-Z-Q'- wherein Q is covalently bonded to the hydrophilic polymer chain either directly or by means of a pendant alkyl or other functional group and Q' is covalently bonded to the cylodextrin at the 2, 3 or 6 position thereby replacing either an $OR_1$, an $OR_2$ or an $OR_3$ group respectively; Q and Q' are independently members selected from the group consisting of $NR_4$, S, O, CO, CONH, and COO; Z is a member selected from the group consisting of an alkylene disulfide, [—$(CH_2)_aS$—$S(CH_2)_a$—], an alkylene [—$(CH_2)_a$—], an alkylene oxide (—$[(CH_2)_aO]_b(CH_2)_a$—), or a peptide linker, where a is an integer of 1 to 10 and b is an integer of 1 to 20; $R_1$, $R_2$, $R_3$ and $R_4$ are independently members selected from the group consisting of H, alkyl ($C_{n'}H_{2n'+1}$), alkenyl ($C_{n'+1}H_{2(n'+1)-1}$) or acyl ($C_{n'}H_{2n'+1}CO$) where n' is an integer of 1 to 16; q is an integer of 5, 6 or 7; w is an integer such as to provide between 2 and 15 cyclodextrin units per 20 KD polyethylene glycol (PEG) backbone chain, and m and n are integers sufficient that when combined with w they represent a polyethylene oxide polymeric chain having a molecular weight of 5,000 to 70,000 with the proviso that monomeric units on the biocompatible polymer backbone containing the grafted cyclodextrin units represented by w do not have to be consecutively joined but may be randomly or uniformly distributed along the polymer backbone.

8. The cyclodextrin grafted biocompatible polymer of claim 7 where Q is C(O)NH, Q' is $NR_4$ and a is 2.

9. The cyclodextrin grafted biocompatible polymer of claim 7 where Z is —$(CH_2)_2S$—$S(CH_2)_2$; $R_4$ is $C_2H_5$; $R_1$ is $C_2H_5$; $R_2$ is H and $R_3$ is $C_2H_5$.

10. A cyclodextrin grafted biocompatible polymer having the formula 3

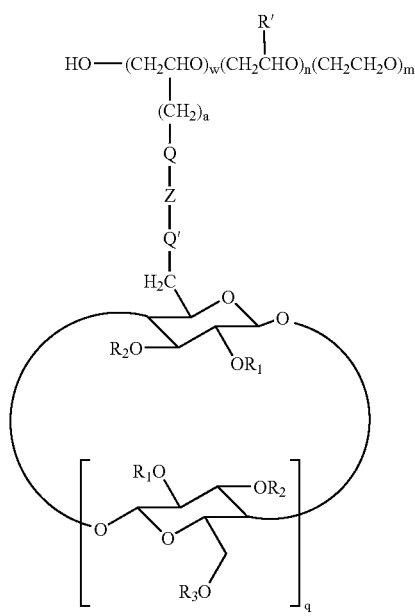

wherein R' is H or a targeting moiety; Q is covalently bonded to the hydrophilic polymer chain either directly or by means of a pendant alkyl or other functional group and Q' is covalently bonded to the cylodextrin at the 2, 3 or 6 position thereby replacing either an $OR_1$, an $OR_2$ or an $OR_3$ group respectively; Q and Q' are independently members selected from the group consisting of $NR_4$, S, O, CO, CONH, and COO; Z is a member selected from the group consisting of an alkylene disulfide, [—$(CH_2)_aS$—$S(CH_2)_a$—], an alkylene [—$(CH_2)_a$—], an alkylene oxide (—$[(CH_2)_aO]_b(CH_2)_a$—), or a short chained peptide, where a is an integer of 1 to 10 and b is an integer of 1 to 20; $R_1$, $R_2$, $R_3$ and $R_4$ are independently members selected from the group consisting of H, alkyl ($C_{n'}H_{2n'+1}$), alkenyl ($C_{n'+1}H_{2(n'+1)-1}$) or acyl ($C_{n'}H_{2n'+1}CO$) where n' is an integer of 1 to 16; q is an integer of 5, 6 or 7; w is an integer such as to provide between 2 and 15 cyclodextrin units per 20 KD polyethylene glycol (PEG) backbone chain, and m and n are integers sufficient that when combined with w they represent a polyethylene oxide polymeric chain having a molecular weight of 5,000 to 70,000 with the proviso that monomeric units on the hydrophilic polymer chain containing the cyclodextrin units represented by w do not have to be consecutively joined but may be randomly or uniformly distributed along the polymer chain.

11. The cyclodextrin grafted biocompatible polymer of claim 10 where Q is C(O)NH, Q' is $NR_4$ and a is 2.

12. The cyclodextrin grafted biocompatible polymer of claim 10 where Z is —$(CH_2)_2S$—$S(CH_2)_2$—; $R_4$ is $C_2H_5$; $R_1$ is $C_2H_5$; $R_2$ is H and $R_3$ is $C_2H_5$.

13. A composition comprising a cyclodextrin grafted biocompatible polymer of claim 1 and an active agent.

14. The composition of claim 13 wherein the active agent is a hydrophobic drug, a protein or peptide drug, a nucleic acid or an oligonucleotide.

15. The composition of claim 13 wherein the active agent is paclitaxel.

16. A composition comprising a cyclodextrin grafted biocompatible polymer of claim 7 and an active agent.

17. The composition of claim 16 wherein the active agent is a hydrophobic drug, a protein or peptide drug, a nucleic acid or an oligonucleotide.

18. The composition of claim 16 wherein the active agent is paclitaxel.

19. A composition comprising a cyclodextrin grafted biocompatible polymer of claim 10 and an active agent.

20. The composition of claim 19 wherein the active agent is a hydrophobic drug, a protein or peptide drug, a nucleic acid or an oligonucleotide.

21. The composition of claim 19 wherein the active agent is paclitaxel.

22. A method for delivery of an active agent to a warm blooded animal comprising administering the composition of claim 13 to said warm blooded animal.

23. The method of claim 22 wherein the active agent is a hydrophobic drug, a protein or peptide drug, a nucleic acid or an oligonucleotide.

24. The method of claim 22 wherein the method is for the treatment of cancer, wherein the active agent is paclitaxel, and the composition is administered in an amount effective to treat cancer.

25. A method for delivery of an active agent to a warm blooded animal comprising administering the composition of claim 16 to said warm blooded animal.

26. The method of claim 25 wherein the active agent is a hydrophobic drug, a protein or peptide drug, a nucleic acid or an oligonucleotide.

27. The method of claim 25 wherein the method is for the treatment of cancer, wherein the active agent is paclitaxel, and the composition is administered in an amount effective to treat cancer.

28. A method for delivery of an active agent to a warm blooded animal comprising administering the composition of claim 19 to said warm blooded animal.

29. The method of claim 28 wherein the active agent is a hydrophobic drug, a protein or peptide drug, a nucleic acid or an oligonucleotide.

30. The method of claim 28 wherein the method is for the treatment of cancer, wherein the active agent is paclitaxel, and the composition is administered in an amount effective to treat cancer.

* * * * *